(12) United States Patent
Teschner et al.

(10) Patent No.: US 12,369,810 B2
(45) Date of Patent: Jul. 29, 2025

(54) PROCESS AND SYSTEM WITH A MEASURING DEVICE AND AN ANALYSIS DEVICE FOR PROCESSING DATA

(71) Applicant: Drägerwerk AG & Co. KGaA, Lübeck (DE)

(72) Inventors: Eckhard Teschner, Lübeck (DE); Frank Ralfs, Lübeck (DE)

(73) Assignee: DRÄGERWERK AG & CO. KGAA, Lübeck (DE)

( * ) Notice: Subject to any disclaimer, the term of this patent is extended or adjusted under 35 U.S.C. 154(b) by 413 days.

(21) Appl. No.: 18/081,826

(22) Filed: Dec. 15, 2022

(65) Prior Publication Data

US 2023/0190127 A1 Jun. 22, 2023

(30) Foreign Application Priority Data

Dec. 22, 2021 (DE) ..................... 10 2021 134 348.8

(51) Int. Cl.
*A61B 5/0536* (2021.01)
*A61M 16/00* (2006.01)

(52) U.S. Cl.
CPC ......... *A61B 5/0536* (2013.01); *A61M 16/024* (2017.08); *A61M 2230/46* (2013.01)

(58) Field of Classification Search
CPC .......................... A61B 5/0536; A61M 16/024
USPC ......................................................... 382/131
See application file for complete search history.

(56) References Cited

U.S. PATENT DOCUMENTS

| 4,486,835 A | 12/1984 | Bai et al. |
| 5,184,624 A | 2/1993 | Brown et al. |
| 5,311,878 A | 5/1994 | Brown et al. |
| 5,769,082 A * | 6/1998 | Perel ...................... A61B 5/029 600/484 |
| 5,807,251 A | 9/1998 | Wang et al. |
| 6,236,886 B1 | 5/2001 | Cherepenin et al. |
| 9,713,689 B2 | 7/2017 | Brochard et al. |
| 2012/0272961 A1 * | 11/2012 | Masic ............... A61M 16/0051 128/204.23 |
| 2013/0174846 A1 * | 7/2013 | Stenqvist ............... A61B 5/085 128/204.23 |

(Continued)

FOREIGN PATENT DOCUMENTS

| DE | 102016011161 A1 | 3/2018 |
| DE | 102017007224 A1 | 2/2019 |

(Continued)

OTHER PUBLICATIONS

Costa, Eduardo LV, et al. Bedside Estimation of Recruitable Alveolar Collapse and Hyperdistension by Electrical Impedance Tomography. In: Applied Physiology in Intensive Care Medicine 1. Springer, Berlin, Heidelberg, 2012. S. 165-170.

*Primary Examiner* — Allen H Nguyen

(74) *Attorney, Agent, or Firm* — McGlew and Tuttle, P.C.

(57) ABSTRACT

An apparatus and process (100) for processing data (101, 102, 103) obtained by an imaging technique enables an improvement of a determination of quality and quantity of ventilation of the lungs. By including a correction data set KDS determined during one or more inhalation phases, it is determined which effects result from adjustments of pressure levels ($PEEP_A$, $PEEP_B$) (81, 82) during ventilation. The result of the determination is provided as an output signal (900).

28 Claims, 8 Drawing Sheets

(56) References Cited

U.S. PATENT DOCUMENTS

| | | | |
|---|---|---|---|
| 2019/0038173 A1 | 2/2019 | Gärber et al. | |
| 2021/0016035 A1* | 1/2021 | Euliano, II | A61B 5/7282 |
| 2021/0290883 A1* | 9/2021 | Dong | A61M 16/00 |
| 2022/0218928 A1* | 7/2022 | Liu | A61M 16/024 |

FOREIGN PATENT DOCUMENTS

| | | |
|---|---|---|
| DE | 102020000846 A1 | 8/2020 |
| DE | 102021005908 A1 | 6/2022 |
| EP | 1292224 A1 | 3/2003 |
| WO | 0193760 A1 | 12/2001 |

\* cited by examiner

PROCESS AND SYSTEM WITH A MEASURING DEVICE AND AN ANALYSIS DEVICE FOR PROCESSING DATA

CROSS REFERENCE TO RELATED APPLICATIONS

This application claims the benefit of priority under 35 U.S.C. § 119 of German Application 10 2021 134 348.8, filed Dec. 22, 2021, the entire contents of which are incorporated herein by reference.

TECHNICAL FIELD

The present invention relates to a process and a system for processing data from an analysis device and measurement data which are obtained or determined during ventilation of a patient. The measurement data may be obtained and provided by a measurement system suitable for a metrological acquisition of physical measurement data. The analysis device may preferably be configured as a system or device for electroimpedance tomography (EIT), which provides the data as image data or data sets of image data as a data set of EIT data. In addition to image data, the EIT-data may also comprise impedance values, impedance changes, impedance time courses. Devices for electroimpedance tomography (EIT) are known from the prior art. These devices are configured and intended to generate an image, multiple images or a continuous image sequence from signals obtained using impedance measurements and data and data streams obtained therefrom. These images or image sequences show differences in the conductivity of various body tissues, bones, skin and body fluids and organs, which can then be used by a user to support a diagnosis of diseases or medical conditions.

BACKGROUND

For example, U.S. Pat. No. 6,236,886 describes an electrical impedance tomograph system with an arrangement of several electrodes, current supply at at least two electrodes and a process with an algorithm for image reconstruction for determining the distribution of conductivities of a body such as bones, skin and blood vessels in a principal embodiment with components for signal acquisition (electrodes), signal processing (amplifier, A/D converter), current supply (generator, voltage-current converter, current limitation) components for control (μC). With the help of visualizations, further applications are possible for the detection of various forms of lung disease.

U.S. Pat. No. 2,019,038 173 A describes an apparatus for determining differential end-expiratory impedance values based on impedance tomography data of regions of the lungs of a living being. The device enables an evaluation (WIN/LOSS) of changes in regions of the lungs with respect to overdistension or collapse by means of differential indices.

In U.S. Pat. No. 5,807,251 it is stated that in the clinical application of EIT it is known to provide a set of electrodes which are arranged at a certain distance from each other, for example around the chest of a patient in electrical contact with the skin, and to apply an electrical current or voltage input signal alternately between different or all of the possible pairs of electrodes arranged adjacent to each other. While the input signal is applied to one of the pairs of mutually adjacent electrodes, the currents or voltages between each mutually adjacent pair of the remaining electrodes are measured and the measurement data obtained is processed in a known manner to obtain and display on a display screen a representation of the distribution of electrical resistivity over a cross-section of the patient around which the electrode ring is disposed.

U.S. Pat. No. 5,184,624 shows an arrangement of a plurality of electrodes for an electroimpedance measurement on a body, with feeding of electric current via a pair of electrodes into the body and the detection of voltage potentials on the body via the remaining pairs of electrodes. In this case, two electrodes are successively selected from the plurality of electrodes to be the feeding electrode pair in the manner of a circuit around the body, and a plurality of the remaining electrodes are used as electrode pairs for detecting the voltage potentials.

U.S. Pat. No. 4,486,835 describes an apparatus for electroimpedance tomography in which electrical signals are applied to a body at selected first electrode pairs and electrical signals are detected at selected second electrode pairs in a predetermined sequence by means of a multiplexing device and are passed on to a calculation device coupled to the multiplexing device for determining electrical properties of a plurality of local regions of the body. In this process, these local regions are arranged in a 3-dimensional imaging grid structure in the body and the electrical conductivity at the plurality of local regions is continuously updated in an iterative process.

U.S. Pat. No. 5,311,878 describes a process and apparatus of electroimpedance tomography for real-time imaging. Impedance measurement signals from two selected adjacent electrodes of electrodes arranged around a thorax are supplied to digital signal processing with simultaneous injection of an injection current into selected electrodes and real-time images are generated by means of computer-based reconstruction.

EP 1 292 224 B2 describes a process and apparatus for displaying data obtained by electrical impedance tomography. Various special modes such as relative mode, absolute mode, perfusion mode, time constant mode and a regional spirometry mode are described. The different modes are used to distinguish different lung conditions.

U.S. Pat. No. 9,713,689 B2 discloses a ventilator for automated assessment of a patient on therapy with a positive end-expiratory pressure. The ventilator enables respiratory support for a patient and delivery of therapy with measurement of an end-expiratory lung volume (EELV) of the patient at a first end-expiratory pressure and measurement of an end-expiratory lung volume at a second end-expiratory pressure. Based on a calculation of a difference between the first end-expiratory lung volume and the second end-expiratory lung volume, an index indicative of the patient's response to PEEP therapy is determined including a functional residual capacity (FRC) of the patient.

SUMMARY

An object of the present invention is to provide a process and a system for data processing of data obtained by means of a measuring device and an analyzing device during the performance of ventilation, in order to perform a determination of a ventilation situation (ventilation) of the lungs.

These and other objects are attained by a system having features according to the invention.

A further solution of the problem results from a process having features according to the invention.

Advantageous embodiments of the invention will be apparent from this disclosure and will be explained in more detail in the following description with partial reference to the figures.

A system according to the invention for processing data obtained or provided by means of a measuring device and an analysis device, can process data in such a way that a difference between data assignable to a second situation and data assignable to a first situation can be determined and provided by the control unit as an output signal indicating the difference by means of a data output unit. By including correction data ascertained during one or more inhalation phases, it is possible to determine which effects arise with regard to a situation of lungs of a living being due to different levels in exhalation phases during ventilation between the first and second situation.

Some of the terminology used in the context of this patent application is explained in more detail below. The ventilation pressure is referred to as an inspiratory ventilation pressure $P_{insp}$ for phases of inspiration, and the ventilation pressure is referred to as an expiratory ventilation pressure $P_{exp}$ for phases of expiration. For the ventilation pressure at the end of the expiratory phase, the term "positive end expiratory pressure" (PEEP) is used. For the purposes of the present invention, an observation period is to be understood as a period of time in a time course. The beginning and end of such an observation period are given by events which are given by the properties of respiration or ventilation. Examples of respiration-specific periods of consideration include a respiratory cycle, multiple respiratory cycles, parts of respiratory cycles such as inspiration, inspiratory pause, expiration, expiratory pause, and also parts of one or more respiratory cycles, e.g. multiple inspirations, multiple expirations. Further periods of consideration, especially in artificial ventilation, may be certain pressure levels such as plateau pressure or PEEP pressure (PEEP) or time periods corresponding to certain characteristics of ventilation modes (e.g. Bi-Level Positive Airway Pressure, BiPAP, Continuous Positive Airway Pressure CPAP). In the context of the present invention, EIT-data means the following signals or data:

EIT raw data, i.e. measurement signals such as voltages or currents acquired with an EIT device by means of a group of electrodes or by means of an electrode belt, assigned to electrodes or groups of electrodes or to positions of electrodes or groups of electrodes on an electrode belt.

EIT image data, i.e. data or signals obtained from the raw EIT data using a reconstruction algorithm and reflecting local impedances, impedance differences or impedance changes of areas of the lungs or areas of the lungs and heart of a patient.

Classified EIT data, i.e. EIT image data or signals pre-sorted or pre-classified according to predefined criteria.

The system according to the invention has
a measuring device
an analysis device
a data input unit
a control unit
a data output unit.

The measuring device is configured for the metrological acquisition of physical measurement data. The measuring device is configured for the metrological acquisition of pressure measurement values of a ventilation pressure or a time course of a ventilation pressure.

The analysis device is preferably configured as an EIT system and comprises an electroimpedance tomography device, an electroimpedance tomography data processing arrangement comprising a data input unit and a display device. The electroimpedance tomography device has an electrode arrangement with a plurality of electrodes, operating electronics, a measured value acquisition and evaluation unit and a data processing and calculation unit.

The electrode arrangement is placed on or around the thorax of a patient. At least two of the electrodes of the electrode arrangement are configured to feed an alternating current or an alternating voltage, and at least two of the electrodes of the electrode arrangement are configured to detect measurement signals. The operating electronics are configured to feed the alternating current or the alternating voltage into the electrodes. The measured value acquisition and evaluation unit is configured to acquire the measurement signals at the electrodes. The operating electronics and the measured value acquisition and evaluation unit are configured to feed the alternating current or the alternating voltage to at least two of the electrodes and to acquire measurement signals at at least two electrodes of the electrode arrangement in such a way that, in a continuous sequence, in each case the other two electrodes are successively selected from the electrode arrangement for feeding the alternating current or the alternating voltage and the measurement signals are acquired with at least two electrodes of the electrode arrangement. The data processing and calculation unit is configured to generate, by means of a reconstruction algorithm, from the measurement signals a data set of signals over a signal course of at least one location lying within an observation period and to provide this to the data input unit.

Data processing and analysis can be divided into the following steps:
Provision of a first set of measurement data by the measurement device,
Provision of a second set of data by the analysis device,
Provision of a third set of data by the analysis device,
Carrying out a comparison with a determination of a difference based on the second and third data sets,
Inclusion of correction data in the comparison to determine the difference based on the first, second and third data sets,
Generation of an output signal, which indicates the determined difference as a result.

In the system according to the invention, these steps of processing data are carried out by the control unit and are repeated continuously.

The processed data are provided as output signals in a suitable manner, preferably for an image display as well as for further processing or evaluation by a data output unit.

The provision of the data sets may be performed by means of a data input unit, and the provision of the output signal may be performed by means of the data output unit.

The processing of the data takes place as a data processing with sorting, analysis, data comparison and data selection by a control unit.

For this purpose, the control unit has elements for data processing, calculation and sequence control, such as microcontrollers (µC), microprocessors (µP), signal processors (DSP), logic modules (FPGA, PLD), memory modules (ROM, RAM, SD-RAM) and combination variants thereof, for example in the form of an "embedded system", which are jointly configured and adapted to one another and are configured by programming to carry out the data processing.

The data input unit is configured to provide the data sets or to read in data or data sets by means of an interface. The data input unit preferably has interface elements such as, for example, amplifiers, A/D converters, components for over-voltage protection (ESD protection), logic elements and further electronic components for wired or wireless reception of the data and signals, and adaptation elements such as code or protocol conversion elements for adapting the signals and data for further processing in the control unit.

The data output unit is configured to generate and provide the output signal. The output signal is preferably configured as a video signal (e.g. video out, component video, S-video, HDMI, VGA, DVI, RGB) for enabling a graphical, numerical or pictorial representation of the at least one characteristic location-specific and perfusion-specific variable for the observation period on a display unit connected to the output unit by wireless or wired means (WLAN, Bluetooth, WiFi) or on the output unit itself.

The system according to the invention is configured for processing data obtained during the performance of a ventilation by a ventilation device by means of an analysis device suitable for a determination of a lung condition and measurement data obtained by means of a measurement device suitable for a metrological acquisition of physical measurement data.

For this purpose, the system according to the invention comprises a data input unit, a data output unit and a control unit. The system is configured by means of the data input unit to acquire or receive data from the measuring device. The data of the measuring device is assignable to situations with predetermined pressure levels and can be provided as a first set of measurement data over a time course of a period of observation during a ventilation of a living being. The system is configured to acquire or receive data from the analysis device by means of the data input unit. The data of the analysis device is assignable to a first situation and can be provided as a second set of data over a time course of a viewing period during a ventilation of a living being.

The system is configured to provide a control signal by means of an interaction of a control unit and a data output unit.

Using the control signal, the control unit can initiate an adjustment by a predetermined pressure difference from a first positive end-expiratory pressure level ($PEEP_A$) to a second positive end-expiratory pressure level ($PEEP_B$) at a ventilation device.

The system is configured to acquire or receive further data from the analysis device by means of the data input unit. The further data of the analysis device is assignable to a second situation and can be provided as a third data set of further data over a time course of a period of observation during a ventilation of a living being.

The control unit is adapted to process data and is provided for processing data. The control unit is adapted to process the first set of data, the second set of data and the third set of data.

By means of a comparison, a difference DZ between the further data of the second situation and the data of the first situation can be determined. The control unit is adapted to include in the comparison a correction data set KDS for correcting the difference DZ. This results in a corrected difference $DZ_K$.

In an alternative embodiment, a difference DZ between signals of the second situation and signals of the first situation can also be determined on the basis of current or voltage signals, which are provided, for example, by an electrode arrangement of an EIT system. This difference determined on the basis of the signals also enables an evaluation as to which effect was caused by the adjustment of the end-expiratory pressure. On the basis of the signals it can be determined, for example, whether—for example in the case of an increase in end expiratory pressure—the lungs or which areas of the lungs have benefited not only directly from the increase in volume caused by the increase in pressure, and whether and in which areas of the lungs there has been an increase in reopened lung areas (pulmonary sacs, alveoli) which were previously not available for gas exchange. The correction data set KDS comprises data elements of the second data set, which indicate certain pressure situations $P_1$, $P_2$ at a time $t_1$, $t_2$ within the observation period of a ventilation pressure. The control unit is adapted to determine an output signal based on the comparison, based on the difference DZ, or based on the corrected difference $DZ_K$. The output signal may indicate the difference DZ and/or the corrected difference $DZ_K$. The control unit is adapted to provide the output signal by means of the data output unit.

In a preferred embodiment of the system, data elements in the first set of data comprise data elements which define certain pressure situations $P_1$, $P_2$ at times $t_1$, $t_2$ on a rising slope of an inspiratory ventilation pressure $P_{insp}$.

In a preferred embodiment of the system, data elements in the first data set comprise specific pressure situations $P_1$, $P_2$ at time points $t_1$, $t_2$ on a falling slope of an expiratory ventilation pressure $P_{exp}$.

Preferably, the determined pressure situations $P_1$, $P_2$ respectively indicate states in the course of ventilation at which volume changes occur in the lungs of the living being, which can be determined by means of the analysis device, so that, for example, a certain pressure situation during an inhalation phase, for example a pressure level $P_1$ during a rising slope of the inspiratory ventilation pressure $P_{insp}$ corresponds with a volume change in the lungs. The same applies in a transferable manner to exhalation, where, for example, a certain pressure situation during an exhalation phase, for example a pressure level $P_2$, during the falling slope of the expiratory ventilation pressure $P_{exp}$ corresponds with a volume change in the lungs.

In a preferred embodiment of the system, the analysis device is suitable and configured for imaging the lungs of a living being. In a particularly preferred embodiment of the analysis device, imaging of the lungs can be performed by systems such as an electrical impedance tomography device or EIT systems. Imaging of the lungs may further be performed by systems such as a magnetic resonance imaging device. Imaging of the lungs may be performed by systems such as a computed tomography device. Imaging of the lungs may be performed by systems such as an ultrasound imaging device. Electrical impedance tomography (EIT) devices have distinct advantages over magnetic resonance imaging (MRI) and also computed tomography (CT) devices, essentially with respect to the following aspects:
  EIT has a real-time functionality
  EIT does not require coupling to ECG
  EIT does not require a contrast agent
  EIT allows for a trend display and analysis
With regard to sonographic devices for cardiological, angiological, prenatal or neonatal imaging, it should be noted that their use is limited to temporary examinations, since the transducer in combination with the contact gel must be guided by the user and the alignment of the transducer as well as the function of the contact gel must be observed visually by the user continuously during the examination. This results in the following advantages:
  EIT does not require contact gel
  EIT does not require continuous function monitoring by the user The electroimpedance tomography (EIT) is therefore, in contrast to the mentioned further medical devices suitable for imaging (X-ray devices, computer tomographs, magnetic resonance tomographs, sonographic devices), suitable for a continuous and permanent imaging, in particular of lungs as well as of lungs and heart, without causing significant physical strain or discomfort for the patient.

In a preferred embodiment of the system, the analysis device is configured as a device suitable for determining the volume of the lungs of a living being. A device suitable for a volume determination of the lungs of a living being can be formed by a device for spirometry or can be formed by measurement and analysis functions of a device for ventilation of a living being, for example an intensive care ventilator, an emergency ventilator, a transport ventilator, a neonatal ventilator or an anesthesia device.

In a preferred embodiment of the system, the first situation is assignable to a first predetermined pressure level $P_1$. In this preferred embodiment, the adjustment of the first positive end-expiratory pressure level ($PEEP_A$) to a second positive end-expiratory pressure level ($PEEP_B$) is initiated by means of the control signal as an increase by the predetermined pressure difference equal to the predetermined pressure level $P_1$ at a ventilation device.

The first predetermined pressure level $P_1$ is preferably determined by a time $t_1$ during a rising slope of the inspiratory ventilation pressure $P_{insp}$. In this preferred embodiment, the control unit performs the comparison as a subtraction of the third data set ($Z_1$) from the second data set ($Z_y$). In this preferred embodiment to determine the corrected difference Dal, the control unit is adapted to perform the correction as a subtractive correction (subtraction of correction data $Z_{K1}$), $DZ_{K1}=(Z_y-Z_1)-Z_{K1}$.

In a further preferred embodiment, the first situation is assignable to a second predetermined pressure level $P_2$. In this further preferred embodiment, the adjustment of the first positive end-expiratory pressure level ($PEEP_A$) by means of the control signal to a second positive end-expiratory pressure level ($PEEP_C$) is initiated as a decrease by the predetermined pressure difference equal to the predetermined pressure level $P_2$ at a ventilation device. The second predetermined pressure level $P_2$ is preferably determined by a time $t_2$ during a falling slope of the expiratory ventilation pressure $P_{exp}$. In this further preferred embodiment, the control unit performs the comparison as a subtraction of the third data set ($Z_2$) from the second data set ($Z_y$). In this further preferred embodiment, to determine the corrected difference $DZ_{K2}$, the control unit is adapted to perform the correction as an additive correction (addition of correction data $Z_{K2}$) $DZ_{K2}=(Z_y-Z_2)+Z_{K2}$.

In a further preferred embodiment of the system, the control unit is configured to perform data acquisition at the predetermined pressure level $P_1$ during the performance of ventilation during the first situation.

In a further preferred embodiment of the system, the control unit is configured to perform data acquisition at the predetermined pressure level $P_2$ during the second situation while performing ventilation.

In a further preferred embodiment, during the first situation, the control unit is configured to perform the data acquisition at the predetermined pressure level $P_1$ on a plateau of the inspiratory ventilation pressure $P_{insp}$ temporally after a rising slope of the inspiratory ventilation pressure $P_{insp}$ during the performance of the ventilation.

In a further preferred embodiment, the control unit is configured to perform the data acquisition during the second situation at the predetermined pressure level $P_2$ on a plateau of the inspiratory ventilation pressure $P_{insp}$ temporally after a rising slope of the inspiratory ventilation pressure $P_{insp}$ during the performance of the ventilation.

In a further preferred embodiment of the system, the measuring device is configured to perform a pressure measurement. In a variant of this further preferred embodiment of the system, the measuring device may form a sub-module of the ventilation device, the analysis device or the measuring device may form a common device with the analysis device.

In a further preferred embodiment of the system, the measuring device is configured to perform a flow measurement and/or to perform a volume measurement. In a variant of this further preferred embodiment of the system, the measuring device may form a sub-module of the ventilation device, the analysis device or the measuring device may form a common device with the analysis device.

In a further preferred embodiment of the system, the control unit is configured to perform the data acquisition as an acquisition of impedance values of selected or representative regions of the lungs and/or as an acquisition of global impedance values over time as a global impedance curve (global impedance course). Selected or representative regions of the lungs in an electroimpedance tomography device are spatially defined areas in 2- or 3-dimensional representations of EIT-data and are often also referred to as ROI (regions of interest) and may be defined or determined, for example, based on the EIT-data as single impedance values or pixels, multiple impedance values or pixels, groups of impedance values or pixels. A global impedance curve may be determined based on the majority of all impedance values or the majority of pixels as well as all impedance values or all pixels by the control unit from the EIT data. In a further preferred embodiment of the system, the control unit is configured to carry out a determination of a representative reference value $Z_0$ or of a fourth data set of reference values as a normalization data set NDS by means of a further data acquisition in the course of time before the first situation in a normalization situation to. In this further preferred embodiment, the control unit is configured to perform a normalization during data acquisition by means of the normalization data set NDS and/or the representative reference value $Z_0$. Such a normalization to a reference value $Z_0$ can, for example, be carried out by the control unit on a regular basis—preferably at a time to at an end-expiratory state in the course of the ventilation, i.e. at the end of an exhalation and before the start of the next subsequent inhalation. Preferably, the control unit can use individual impedance values, groups of impedance values or global impedance values, i.e. values of the global impedance curve for the end expiratory state at time to for this purpose. Such a normalization results in a zeroing, as it were, for the subsequently recorded impedance values or EIT data. Such a zeroing can be performed before or at the beginning of each breath after a certain number of breaths, for example every 5 to 10 breaths, in each case at the beginning by the analysis device, the EIT-system or by the control unit. Such a zeroing during the data acquisition in the EIT system, in particular a repetitive and regular zeroing to always identically defined states in the lungs, in particular to the end-expiratory state in the lungs, in which the exhaled gas has largely completely escaped from the lungs at the end of the exhalation, results in various advantages. For example, the following aspects may be mentioned as advantages:

Reduction of the influence of the quality of electrode coupling and contacting to the skin surface of the living being, in particular variable electrode-to-skin contact resistances, Regular inspection with regard to changes in the contacting of the electrodes and their contact resistances, Identification of changes in the position of the electrodes on the thorax of the living being, Identification of defective electrodes, Possibility to adjust electronic components to a defined state, for example offset correction, adjustment of signal amplification and signal filtering, Possibility to perform comparisons of changes in lung health of a living being on the basis of 2- or 3-dimensional representations of EIT data, on the basis of selected regions (ROI, regions of interest) of the representations or on the basis of the global impedance curve.

In a further preferred embodiment of the system, the control unit is configured to perform a data adjustment to compensate for time differences between the first data set and the second data set in order to synchronize the measuring device and the analysis device in time. Due to the steepness of a rising slope of the inspiratory ventilation pressure $P_{insp}$ both a data acquisition adapted to the slope in terms of sampling rate and a sufficiently good temporal synchronization between the data acquisition of the measuring device and the analysis device are required to ensure that the selected correction data set KDS, which is then used to correct the previously determined difference, contains the predetermined pressure levels $P_1$, $P_2$ of the inspiratory ventilation pressure $P_{insp}$ associated with the corresponding positive end-expiratory pressure levels $PEEP_A$, $PEEP_B$, $PEEP_C$. Synchronization is also particularly relevant in the system when the analysis device and the measurement device are connected via a network (LAN, WLAN). Time delays in the network can be compensated for by data synchronization, preferably with synchronization of the system time or the timers (clocks) in the analysis device and measuring device in the system.

In a further preferred embodiment, the control unit is configured to perform a start of the data acquisition during the second situation after a time delay $T_{Delay}$. The use of the delay time $T_{Delay}$ has the advantage that individual effects or delays in the change in the inflow of respiratory air into regions of the lungs, which may arise to different extents as a result of pressure increases or pressure decreases during ventilation due to different physiological and anatomical characteristics of individual living beings, are not included in the recorded data. Such individual effects or delays such as regional ventilation delays (RVD) of individual areas of the lungs due to flow effects, volume shifts in the respiratory tract or lungs, for example intratidal redistribution of respiratory gases within the lungs are largely completed after the delay time $T_{Delay}$.

In a further preferred embodiment, the control unit is configured to perform the data acquisition during the second situation in a predetermined time interval of 5 to 10 breath cycles after initiation of the second situation with increase to the second positive end-expiratory pressure level ($PEEP_B$). In a further preferred embodiment, the control unit is configured to perform the data acquisition during the second situation in a predetermined time interval of 5 to 10 respiratory cycles after initiation of the second situation with decrease to the third positive end-expiratory pressure level ($PEEP_C$).

In a further preferred embodiment, the control unit is configured to initiate a maneuver with a substantially constant pressure level of the inspiratory ventilation pressure $P_{insp}$ with the first situation on the ventilation device in the course of ventilation. The maneuver may comprise, for example, a duration of a single breath. The substantially constant pressure level may be selected, for example and preferably, at the level of the predetermined pressure level $P_1$, $P_2$.

In a further preferred embodiment, the control unit is configured, while the ventilation is being carried out, to initiate a maneuver at the ventilation device with a plurality of discretely formed pressure levels on a rising slope of the inspiratory ventilation pressure $P_{insp}$. This results in a stepping (gradation) of the rising slope of the inspiratory ventilation pressure $P_{insp}$ with steps (stages) of temporarily and sectionally constant pressure levels. If the pressure measurement of the inspiratory ventilation pressure $P_{insp}$ is carried out at times $t_1$, $t_2$, which lie essentially in the middle in terms of time in a time interval of such pressure level steps, possible error influences caused by imperfect synchronization or synchronization between the analysis device, in particular the EIT system, as well as possible error influences caused by sampling rates not optimally adapted to the steepness of the rising slope of the inspiratory ventilation pressure $P_{insp}$ are of less significance during data acquisition and data processing. Both the largely constant pressure level and the several discretely formed pressure levels on a rising slope of the inspiratory ventilation pressure $P_{insp}$ enable a stable or temporarily stable state of the inspiratory ventilation pressure $P_{insp}$ to be given during the acquisition of the data sets. In this way, sampling rate requirements for data acquisition and requirements for synchronization of data acquisition of the analysis device and the measurement device can be reduced because the steepness of a rising slope of the inspiratory ventilation pressure $P_{insp}$ is not problematic, at least at times, resulting in less influence based on the shape or steepness of the rising slope when acquiring the correction data set KDS.

In a further preferred embodiment of the system, the measuring device is configured as a module or as a component of a device for carrying out ventilation. In such an embodiment, metrological components such as sensors for pressure measurement, flow rate measurement, volume measurement or volume balancing as well as the associated electronics with signal processing, with signal amplification (OP amplifier), signal filtering, signal conversion (A/D converter), signal processing (µC, DSP, FPGA, A/D µC) are arranged in a ventilation device, so that no additional sensors and/or electronics have to be kept ready in a separate measuring device for interaction with the analysis device. A device for ventilating a living being may be configured, for example, as an intensive care ventilator, an emergency ventilator, a transport ventilator, a neonatal ventilator or an anesthesia device.

In a further preferred embodiment, the system with analysis device, measurement device and ventilation device form a common system for ventilation and monitoring of a living being. In addition to spatial integration with common operation, a common system also offers advantages with regard to a coordinated design of the measured value and signal acquisition, signal processing with regard to aspects such as sampling rate, signal filtering, temporal synchronization of the data sets with one another and the possibility of coordinated and/or central control of the interaction of the components of the analysis device, measuring device and ventilation device. The aspects and advantages mentioned for the embodiment with the measuring device as a module or component of a device for carrying out a ventilation also apply in the same and/or transferable manner to the embodiment of the joint system comprising analysis device, measuring device and ventilation device, without requiring special or repeated mention here for the joint system.

In a further preferred embodiment of the system, the control unit is as a component or submodule
in the ventilator,
in the analysis device,
in the measuring device.

The control unit is configured, or the control unit is designed, as a component or module of the common system. The control unit may be arranged centrally in the system or may be configured and arranged in a decentralized or modular manner in the system, both as a module or submodule of analysis device, measurement device or ventilation device. The control unit may be configured with multiple control modules, for example in master/slave configurations in the system. The aspects and advantages which have been mentioned for the embodiments of the common system or the embodiment with the measuring device as a module or component of a device for carrying out a ventilation also apply in the same and/or transferable manner to this embodiment for embodiments of the control unit, without requiring special or repeated mention here for the control unit.

In a further preferred embodiment of the system, in particular the common system, the control unit is adapted to initiate maneuvers with multiple pressure levels of the inspiratory ventilation pressure $P_{insp}$ at the ventilation device while the ventilation is being carried out.

In a further preferred embodiment, the control unit is configured, during a procedure or maneuver to wean a living being from ventilation with a pressure reduction of the inspiratory ventilation pressure $P_{insp}$ and/or expiratory ventilation pressure $P_{exp}$ and/or end expiratory pressure PEEP by the ventilation device in steps or stages during the course of the ventilation, the control unit is configured to control the steps or stages of the pressure reduction by means of the control signal at a level of the stages of the pressure reduction, expiratory pressure PEEP by the ventilation device to initiate the steps or stages of pressure reduction by means of the control signal at a level of the stages of pressure reduction or a time interval between steps of pressure adjustment in dependence on the difference DZ or in dependence on the corrected difference $DZ_K$, $DZ_{K1}$, $DZ_{K2}$ to initiate, coordinate, or control. The control unit may control the implementation of a weaning strategy, the manner of weaning performed individually on the living being, i.e. at what time, with what time interval and in what form, i.e. the order of magnitude ΔP of a pressure adjustment, mostly with lowering of the level of the end expiratory pressure (PEEP), initiated by the control unit by means of the control signal, depending on the difference DZ, $DZ_K$, $DZ_{K1}$, $DZ_{K2}$ determined beforehand and continuously during weaning. Even a return with an increase in the level of end-expiratory pressure (PEEP) to a previous situation on the basis of the determined difference DZ, $DZ_K$, $DZ_{K1}$, $DZ_{K2}$ can thus be carried out in the manner of a control or adaptation loop (adaptive control) by the control unit within the framework of weaning if required and necessary. In particular, an inclusion of the corrected difference $DZ_K$, $DZ_{K1}$, $DZ_{K2}$ offers the advantage of being able to adapt the weaning by the control unit in such a way that the reductions in the level of the end-expiratory pressure (PEEP) carried out for weaning essentially do not result in any permanent loss (LOSS) of lung regions previously participating in the gas exchange. For example, once one of the performed decreases in the level of end-expiratory pressure (PEEP) in a particular lung region (ROI) has caused a loss of lung regions previously participating in gas exchange, i.e. a so-called derecruitment, often also referred to as "de-recruitment", has occurred, the control unit may initiate either a pressure increase above the current pressure level of the end expiratory pressure (PEEP) to the previously given higher pressure level or a pressure increase to a pressure level between the current pressure level and the previously given higher pressure level. Alternatively, or additionally, the control unit may also extend a time period provided in the weaning procedure until the next pressure decrease. In this way, it is possible for the control unit to accompany, secure and/or coordinate a weaning of a living being from ventilation by a ventilation device on the basis of data provided by means of the electroimpedance tomography with data analysis with respect to the current lung condition. An accompaniment may thereby comprise a provision of the results of the data analysis to the user. An assurance may comprise an output of indications or warnings determined by means of the data analysis. A coordination may comprise a control of the ventilation device with regard to the setting of the ventilation pressure, in particular the level of the end expiratory ventilation pressure.

In a further preferred embodiment, the control unit is configured to initiate an increase in the sampling rate at the measuring device and/or at the analysis device at the beginning of the first situation during data acquisition. An increase of the sampling rate, initiated at the measuring device or at the analysis device by the control unit, for example for time intervals in which a rapid increase of the inspiratory ventilation pressure $P_{insp}$ can be expected, thus in particular for a detection of the values and the shape of a rising slope of the inspiratory ventilation pressure $P_{insp}$ results in the advantage that the thus improved temporal resolution of the pressure measurement of the control unit simplifies the identification of the predetermined pressure level $P_1$, or $P_2$ within the first set of data or during the acquisition of the pressure measurement values which are included in the first set of data. A sufficiently high sampling rate results, for example, in the advantage that no method for interpolating or estimating between sampled values on a rising slope of the inspiratory ventilation pressure $P_{insp}$ needs to be implemented in the control unit.

In a further preferred embodiment, the control unit is configured to initiate a maneuver with a predetermined slow inspiratory pressure increase prior to or with the first situation on the ventilation device in the course of ventilation. Such a maneuver is also referred to as a "SLOW inflation maneuver". The course of the rising slope of the inspiratory ventilation pressure $P_{insp}$ results in a maneuver with a predetermined slow inspiratory pressure rise with a reduced slope compared to a conventional pressure controlled ventilation, i.e. the requirements on the sampling rate conditioned by the pressure change per time interval (ΔP/Δt) for the duration of the maneuver represents an alternative to an increase of the sampling rate. Thus, the control unit may, for example, initiate such a maneuver with a predetermined slow inspiratory pressure rise from time to time to provide a less interference-sensitive condition for obtaining reliable pressure readings in the data acquisition of the first set of data for the predetermined pressure situation $P_1$, $P_2$.

The solution to the problem was described with respect to a system. Features, advantages or alternative embodiments mentioned herein are also to be transferred to the claimed process and vice versa. The corresponding objective features of the system are formed in the process by corresponding functional features.

A process according to the invention for a processing of data may be implemented as a sequence of steps
- with a reception of data, which are assignable to situations having predetermined pressure levels,
- with a provision of the measurement data as the first data set,
- with a reception of EIT data in a first situation,
- with a provision of the EIT data as a second data set,
- with a reception of further EIT data in a second situation,
- with a provision of the EIT data as a third data set,
- with a processing of the first, second and third data sets, in order to determine, by means of a comparison including a correction data set KDS, a difference DZ between the further EIT data of the second situation and the EIT of the first situation,
- with a determination and provision of an output signal, indicating the formed difference and/or the corrected difference.

The steps of receiving data with provision of data sets can be implemented, for example, by a data input unit, the steps of processing data can be implemented, for example, by a control unit, the provision of the output signal can be implemented, for example, by an output unit in a similar manner as previously explained and mentioned with respect to the system according to the invention and the embodiments described therefor. Furthermore, the process may also be provided as a computer program or computer program product, so that the scope of protection of the present application also extends to the computer program product and the computer program. Such a computer program product may be advantageously provided on a non transitory computer readable medium.

The embodiments described represent particular embodiments of the system according to the invention, both individually and in combination with one another. Advantages and further embodiments resulting from combinations of several embodiments are nevertheless encompassed by the idea of the invention, even if not all possible combinations of embodiments are set out in detail in each case.

The present invention will now be explained in more detail with the aid of the following figures and the accompanying figure descriptions, without any limitations on the general inventive concept. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
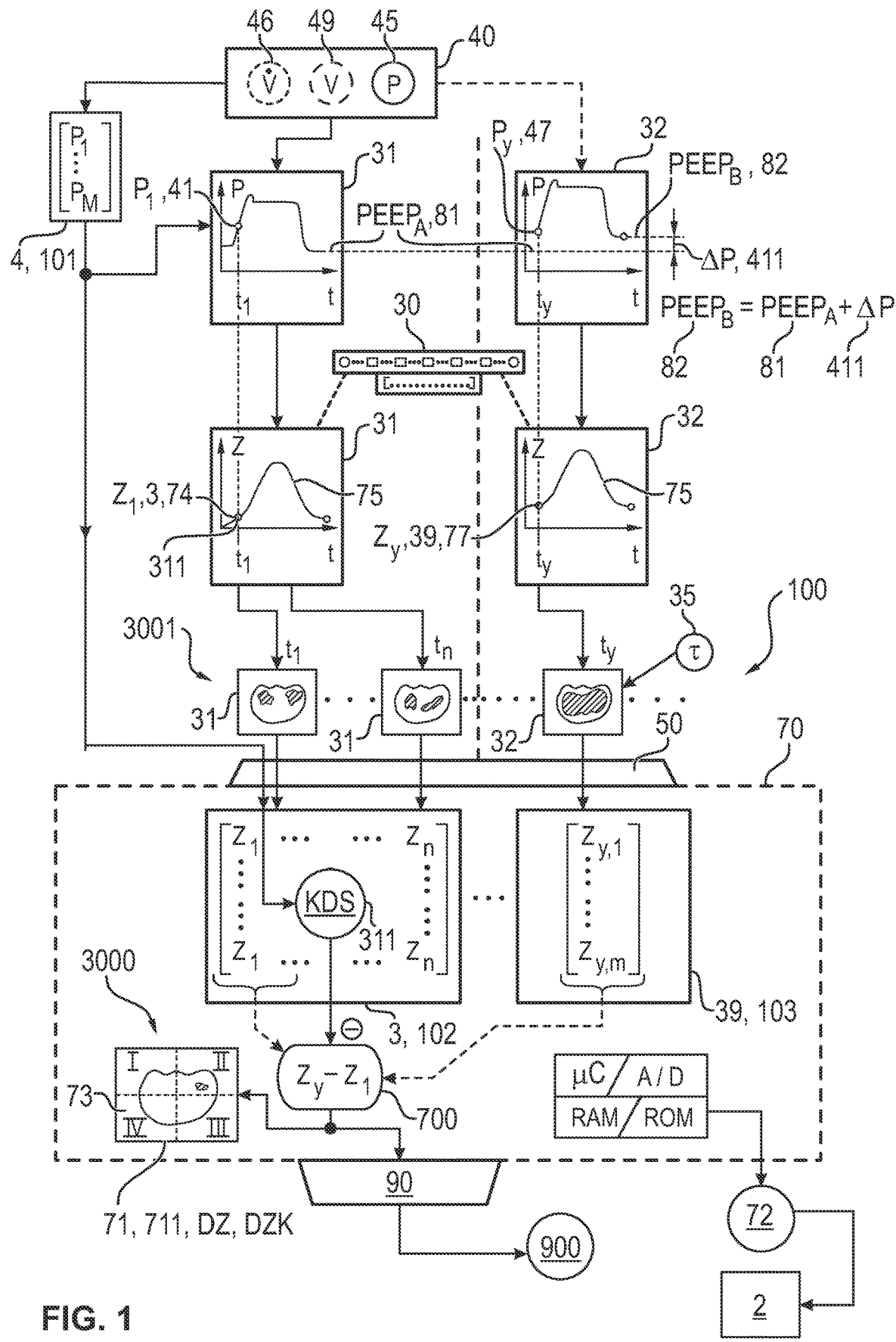
FIG. 1 is a schematic representation of functional elements for the processing of image data or EIT data.
Figure 2:
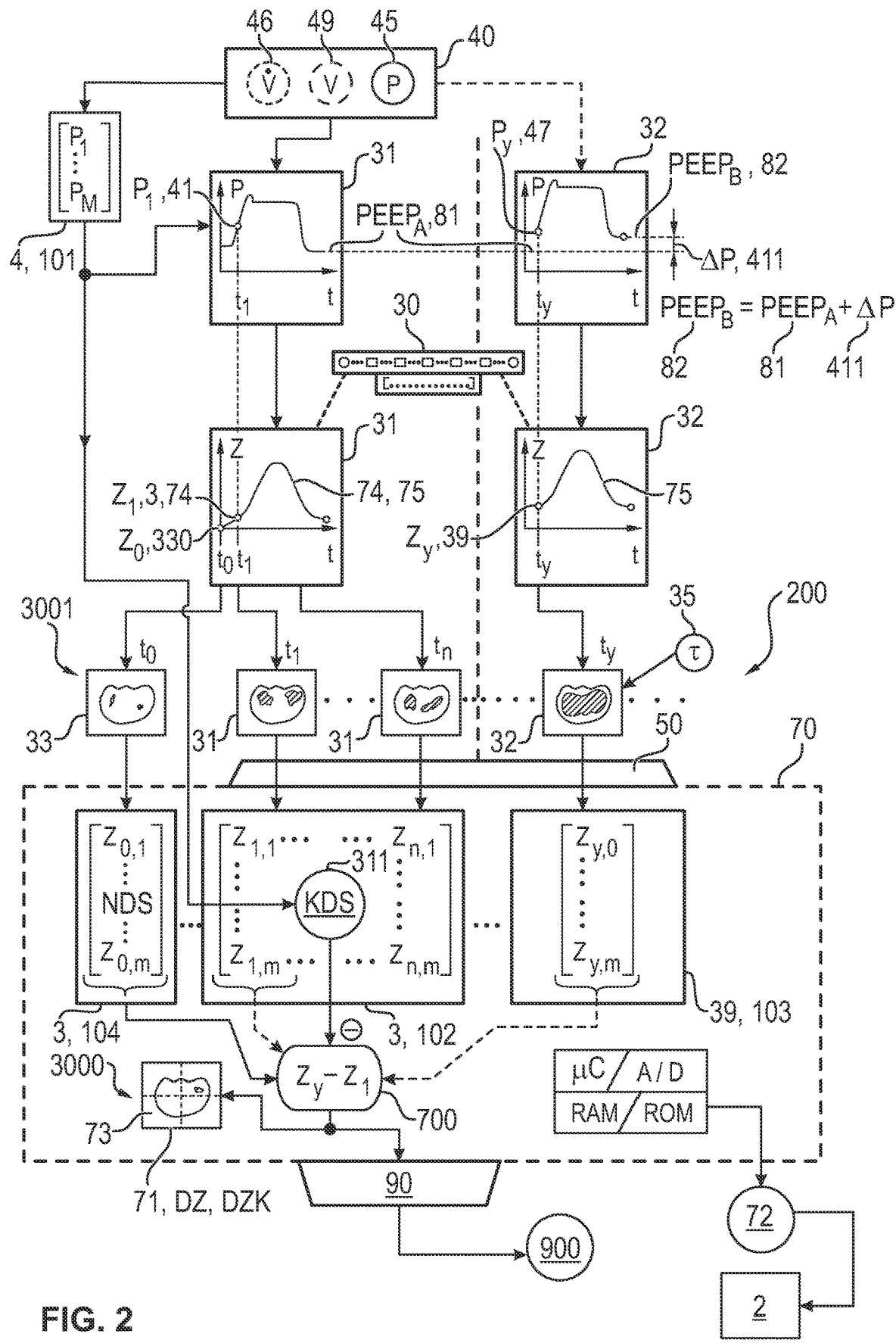
FIG. 2 is a second schematic representation of functional elements.
Figure 3:
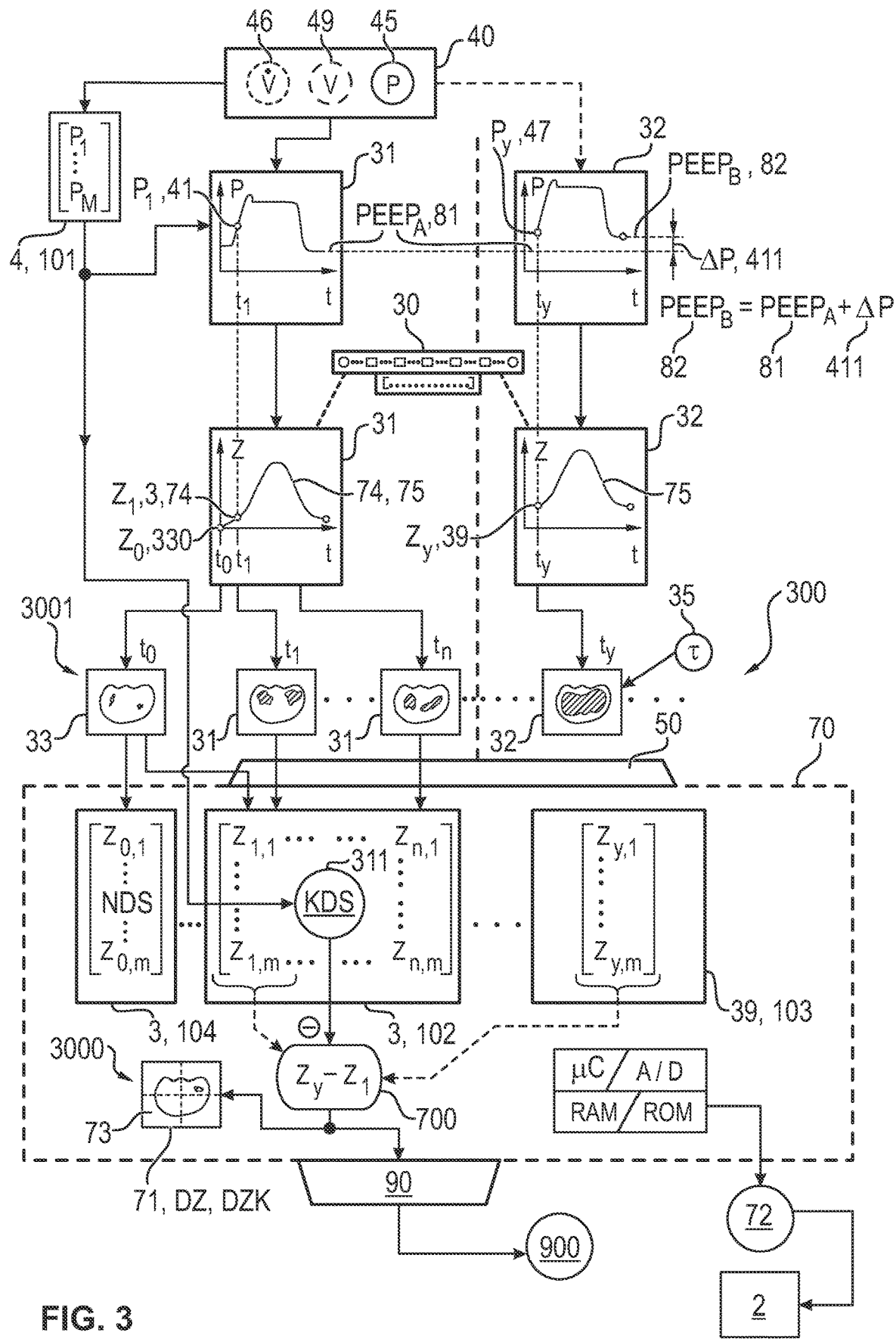
FIG. 3 is a third schematic representation of functional elements.

FIGS. 1-6 describe contexts and sequences for the provision and data processing of data sets 101, 102, 103, 104 in systems 100, 200, 300, 400, 500, 600 with arrangements of functional elements. In the sequences which are described in FIGS. 1-6, the second situation 32 arises temporally after the first situation 31. However, it is intended to be included in the context of the present invention with regard to the temporal assignment of the "first" to the "second" situation that, in the course of the ventilation, the first situation 31 can also arise temporally after the second situation 32. Rather, different positive end-expiratory pressure levels $PEEP_A$ 81, $PEEP_B$ 81, $PEEP_C$ 83 result in the situations 31, 32. In FIGS. 1-3, an increase in the pressure level occurs over time from a first positive expiratory level $PEEP_A$ 81 in the first situation 31 to a second positive expiratory level $PEEP_B$ 82 in the second situation 32.

Figure 4:
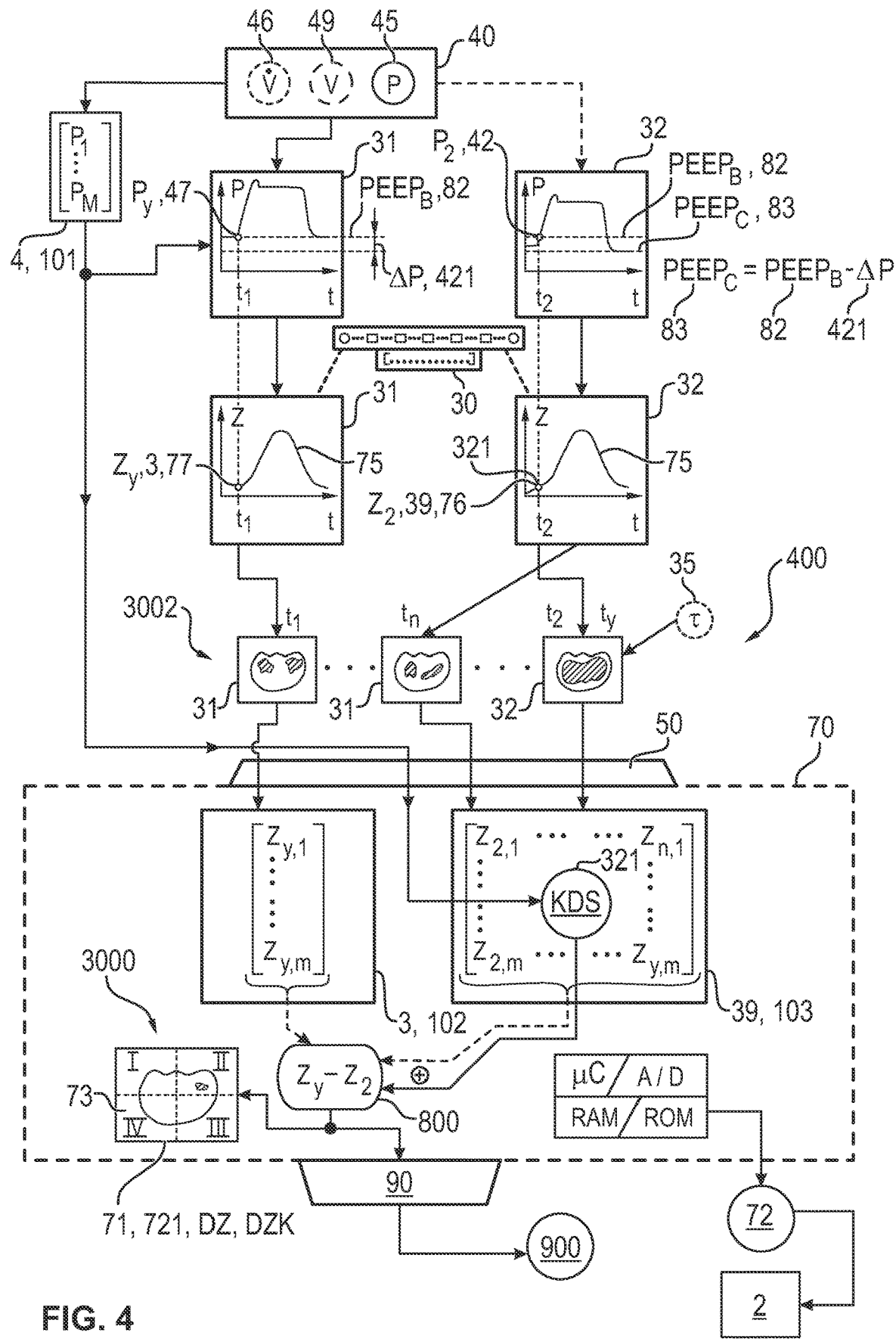
FIG. 4 is a fourth schematic representation of functional elements.
Figure 5:
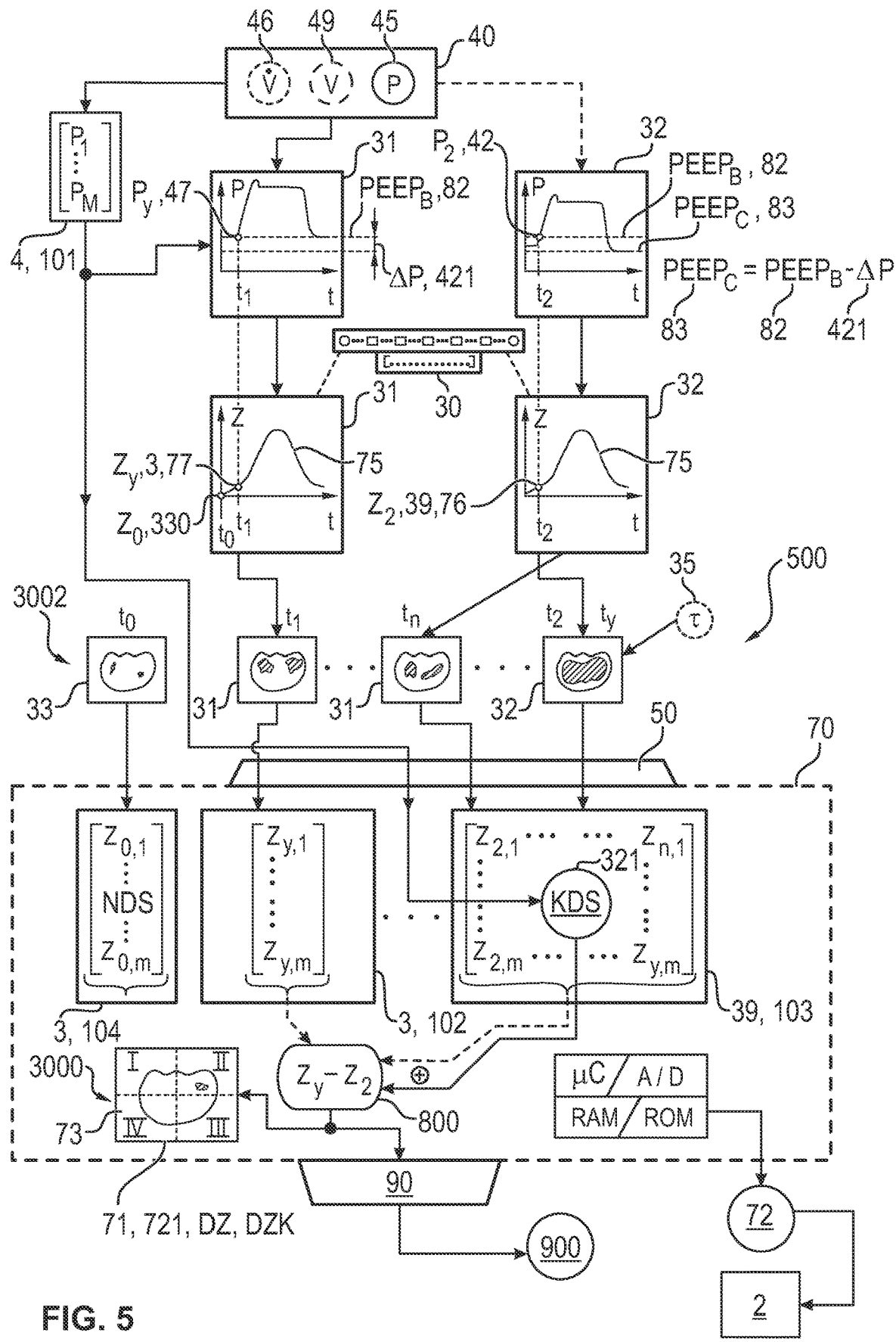
FIG. 5 is a fifth schematic representation of functional elements.
Figure 6:
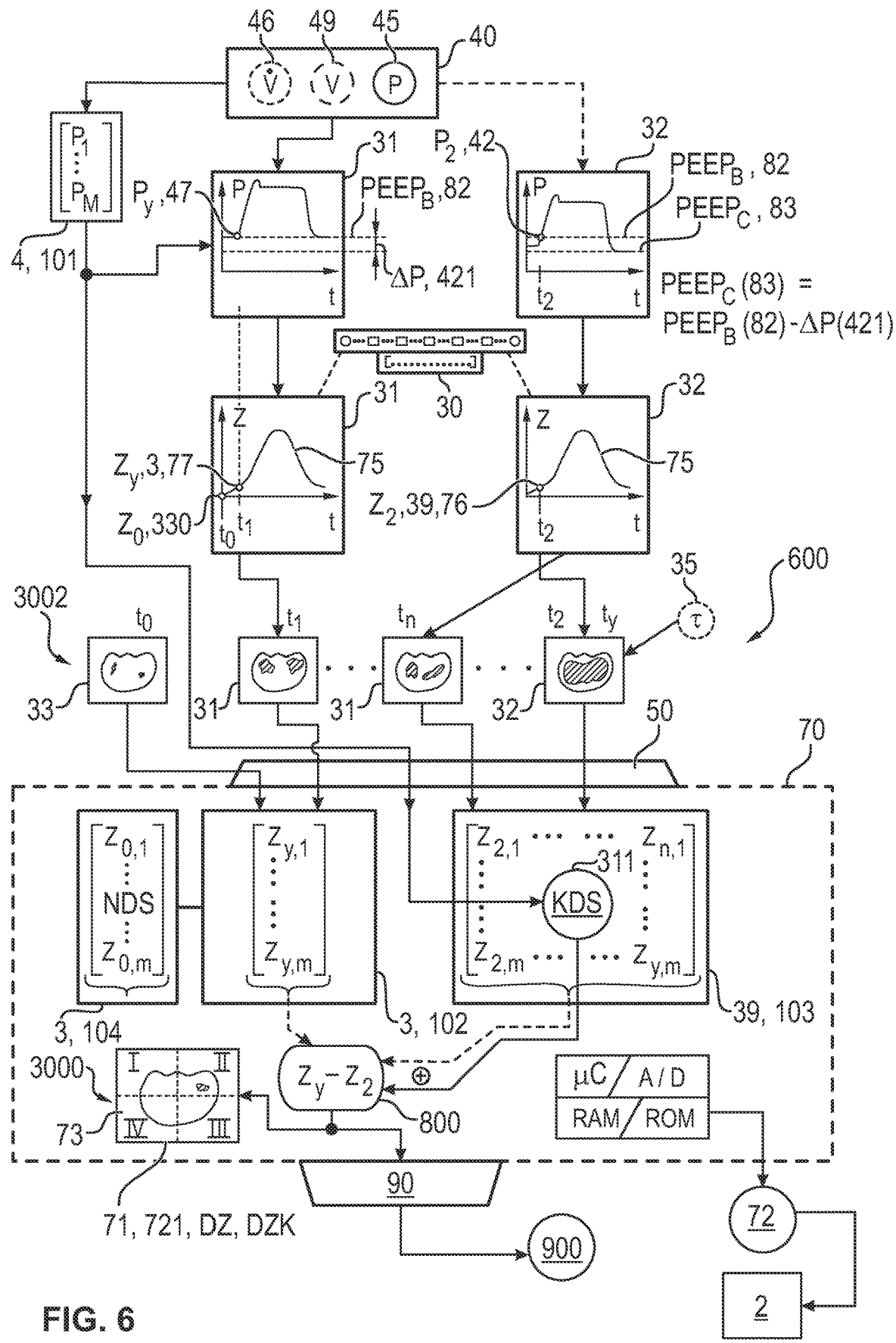
FIG. 6 is a sixth schematic representation of functional elements.

In FIGS. 4-6, the pressure level is lowered over time from a second positive expiratory level $PEEP_B$ 82 in the first situation 31 to a third positive expiratory level $PEEP_C$ 83 in the second situation 32. In FIGS. 1-6, a handling and processing of data sets, configured as first data set 101, second data set 102, third data set 103, fourth data set 104 is performed by a control unit 70. The first data set 101 comprises measurement data 4, in particular pressure measurement values, which are continuously acquired during the operation of measurement device 40, analysis device 30 and ventilation device 2. In particular, the first data set 101 comprises a pressure measurement value $P_1$ 41 acquired in the first situation 31. The second data set 102 comprises impedance values 74 or data of a global impedance curve ZGlobal 75 or image data 3, which were acquired in the first situation 31. The third data set 103 comprises further impedance values 74 or data of a global impedance curve ZGlobal 75 or image data 39 acquired in the second situation 32.

The fourth data set 104 comprises a normalization data set NDS 330 comprising impedance values $Z_0$ or image data 3 acquired in a normalization situation 33.

FIG. 1 shows a system 100 with an arrangement of functional elements for processing image data or EIT data 3 in schematic form.

As basic components, the system 100 comprises a data input unit 50, a control unit 70 and a data output unit 90. A display device—not shown in this FIG. 1 for reasons of clarity—can be connected to the data output unit 90. Such a display device may, for example, comprise display elements, screens or displays for displaying graphics, curves, diagrams or images, or numerical value displays for displaying numerical values, as well as input and operating elements such as switches, buttons, knobs, rotary knobs or a touch-sensitive display (touch screen) as a combination of input and display functionalities. Such a display device may be connected to the data output unit 90 as an internal module or as an external device. By means of the data output unit 90, for example, wireless or wired provision of data to a data network (LAN, WLAN, Ethernet), wireless or wired provision of data for mutual transmission of measured values and control data (e.g. USB, RS232, RS485, FireWire, NMEA 0183, IrDA, Bluetooth, CAN, UMTS [SMS, MMS]) in data exchange with various other external devices (anesthesia or ventilation equipment, ventilation devices, physiological monitors, personal computers, hospital management systems) as well as provision of audio/video data (e.g. Video Out, Component Video, etc.). The device must be able to connect to various external devices (anesthesia or respiratory equipment, physiological monitors, personal computers, hospital management systems) and provide audio/video data (e.g. video out, component video, S-video, HDMI, VGA, DVI, RGB) in various data formats (e.g. MPEG, JPEG, etc.) for connection to the display devices (screens, monitors, tablet PCs).

The data output unit 90 is configured to provide both control signals and/or output signals, for example for representation as numbers, images, diagrams or curves, curve progressions, temporal signal progressions or data sets for display devices (screen, monitor, data display device). For the purposes of the present invention, provision is to be understood as any form of signal or data provision for forwarding, output, display, printing, sending, further processing to further devices or to parts of devices. The control unit 70 performs a variety of tasks within the system 100 such as coordination with the data input unit 50 and with the data output unit 90. The control unit 70 is preferably and for example formed as a central processing unit (CPU, µP) or arrangement of individual microcontrollers (µC). The control unit 70 comprises further units such as memory modules (RAM, ROM, A/D-converter) which are configured for further processing, storage and conditioning of signals or data. The system 100 further comprises various elements for voltage and power supply, which are not shown in this FIG. 1. The connections between the elements and units of the system 100 are only shown schematically in this FIG. 1, for example the essential data connections and data inputs and data outputs are shown, but for reasons of clarity no supply lines and not all connection lines between the elements and units are shown. These units can be configured as individual elements of the control unit 70, but it is included in the sense of the present invention that the control unit 70 can be divided into other sub-modules and can be configured by programming to provide and perform the functions and tasks in the same way or in the same or a different order of processing. A data memory is provided, for example as an arrangement of RAM memory modules, preferably arranged within the control unit 70, and is configured to store and organize data or data sets 101, 102, 103, 104, for example configured as one-dimensional or multi-dimensional arrays, as data sets or sets of data sets as well as results or intermediate results of the data processing (calculations, sorting assignments) for the handling of the data processing. During operation of the system 100, the data input unit 50 reads measurement data 4 from a measurement device 40. In this FIG. 1, the measuring device 40 is exemplarily integrated into the system 100 as an external device or internal module. After being provided or read in, the data input unit 50 holds the measurement data 4 as a first set of data 101 for further processing by the control unit 70. Pressure measurement values 45 and, in an optional manner, further sensor measurement values such as flow rate measurement values 46 or volume measurement values 47 are provided as measurement data 4 of the measurement device 40 via the data input interface 50 of the control unit 70 as the first data set 101. During operation of the system 100, the data input unit 50 reads image data 3 from an analysis device 30. In FIGS. 1-6, this analysis device is configured as an electro-impedance tomography system for an imaging analysis of the lungs of a living being. Such a system is also referred to as an EIT system 30. By means of an electrode arrangement arranged or attached around an upper body of a patient and a sequence of signal injection and acquisition at the electrodes, an EIT-system 30 enables a determination of impedance values with impedance curves and impedance changes of the lungs of the patient. By means of an image reconstruction, the impedance values can be converted into global as well as regional ventilation situations (ventilation) of the lungs and provided as EIT-data 3 in the form of image data or impedance values. In operation, the data input unit 50 reads these EIT data 3 from the EIT system 30. In FIG. 1, the EIT system 30 is exemplarily integrated into the system 100 as an external device or internal module. After reading, the data input unit 50 holds the EIT-data 3 as a second set of data 102 for further processing by the control unit 70. During further operation of the system 100, the data input unit 50 reads further image data 39 from the EIT-system 30 as EIT-data 3 and holds this as a third data set 103 for further processing by the control unit 70. During operation of the system 100, the control unit 70 performs the data processing described below. The pressure measurement value $P_1$ 41 as a data element of the first data set 101 represents a pressure at a time $t_1$ on a rising slope of the inspiratory ventilation pressure $P_{insp}$ in the course of ventilation during a first situation 31, wherein ventilation is performed above a first positive end-expiratory pressure level ($PEEP_A$) 81 by the ventilation device 2. This pressure reading $P_1$ 41 is temporarily stored for a second situation 32, which is temporally subsequent to the first situation, by the control unit 70 as a predetermined pressure difference $\Delta P$ 411. The positive end-expiratory pressure level (PEEP) is raised during the second situation 32 relative to the first positive end-expiratory pressure level ($PEEP_A$) 81 to a second positive end-expiratory pressure level ($PEEP_B$) 82 by the—temporarily stored—pressure difference+$\Delta P$ 411. For this purpose, the control unit 70 uses the predetermined pressure difference+$\Delta P$ 411 in the control signal 72 to raise the pressure of the positive end-expiratory pressure level (PEEP) at the ventilation device 2 according to formula 1.

$$(PEEP_A) + \Delta P = (PEEP_B) \qquad \text{Formula 1}$$

Thus, in the embodiment according to FIGS. 1 to 3, there is a change in the positive end-expiratory pressure level to a higher positive end-expiratory pressure level in the second situation 32 with respect to the first situation 31.

The control unit 70 generates a corresponding control signal 72 in order to initiate an increase of the positive end expiratory pressure level to the second positive end expiratory pressure level ($PEEP_B$) 82 at a ventilation device 2 at the beginning of the second situation 32. For illustration purposes, FIG. 1 schematically depicts pressure/time courses of the measurement device 40 when ventilation is performed at times $t_1$, $t_y$ with associated pressure readings $P_1$ 41, $P_y$ 47. For further illustration, FIG. 1 schematically shows pressure/time courses $t_y$, $Z_1$ 74, $Z_y$ 77, ZGlobal 75 of the EIT system 30 during ventilation at times $t_1$, $t_y$ with associated impedance values $Z_1$ 74, $Z_y$ 77 as well as in the form of multi-dimensional data fields of impedance values $Z_{1,1} \ldots Z_{1,m}$ for the first situation 31 or $Z_{y,1} \ldots Z_{y,m}$ for the second situation 32, respectively. In addition, the EIT data 3, 39 of the two situations 31, 32 are shown schematically in a time sequence of visualizations 3001 of the lungs, whereby in this exemplary graphic embodiment according to FIG. 1 the rather dark surface portions in the schematic images 3001 in transverse view of the lungs correspond in each case to areas with good ventilation, light surface portions then correspondingly correspond to areas with lower ventilation. In practical embodiments of EIT systems 30, the light/dark format is and can mostly be configured in the opposite way. The control unit 70 uses the impedance values $Z_1$ 74 of the first situation 31 and the impedance values $Z_y$ 77 of the second situation 32, or the second data set 102 and the third data set 103, to determine a difference DZ 71 between the two situations 31, 32 by means of a comparison 700 with a subtraction.

$$DZ = Z_y - Z_1 \qquad \text{Formula 2}$$

In addition, it is of interest to determine whether the lungs or which areas of the lungs have not only directly benefited from the increase in volume caused by the (pressure increase) to the second positive end-expiratory pressure level (PEEP$_B$) 82, but whether and in which areas of the lungs there has been an increase in reopened lungs areas (pulmonary sacs, alveoli) that were not previously available for gas exchange. Such a "re-opening" of lungs areas that were not previously available for gas exchange is referred to as recruitment. For this purpose, in the comparison, the pressure situation P$_1$ 41, which corresponds in amplitude or magnitude to the second positive end-expiratory pressure level (PEEP$_B$) 82, is detected at a time t$_1$ on a rising slope of the inspiratory ventilation pressure P$_{insp}$ during an inspiration at the first positive end-expiratory level PEEP$_A$) 81 or is identified by means of an analysis within the first data set 101. Subsequently, a data set is identified by means of an analysis within the second data set 102 at time t$_1$. This identified data set of impedance values is included in the comparison 700 as a correction data set KDS $Z_{K1}$ 311 of impedance values 74 or image data 3 associated to the pressure situation P$_1$ and at the time t$_1$ for some kind of normalization. To normalize the difference DZ 71, the correction data set KDS $Z_{K1}$ 311 is applied according to the following formula 3 by the control unit 70 to determine a so-called "gain" (WIN).

$$WIN = DZK_1 = (Z_y - Z_1) - Z_{K1} \qquad \text{Formula 3}$$

The corrected difference WIN or DZK$_1$ 711 determined in this way may be provided by means of the data output unit 90 as an output signal 900 indicating the difference 711. The output signal 900 may be displayed by means of a schematic visualization 3000. In this schematic visualization 3000, four representative regions I . . . IV (Regions of Interest: ROI) 73 are shown as an example, and in this example, a small dark area region is visible in region II. This small dark area region II represents an area of the lungs that has benefited from an increase in positive end-expiratory pressure level (PEEP$_A$+ΔP=(PEEP$_B$) with an increase in ventilation. This means that in this area II there was not only an increase in volume in the lungs caused directly by the pressure increase, but that regionally there was also an increase in reopened lung areas (pulmonary sacs, alveoli) which were not previously available for gas exchange. The comparison 700 makes it possible to make this difference 71 available to a user in order, for example, to be able to estimate in what way an increase in pressure is suitable for reopening previously collapsed lung regions in addition to the increase in volume. This makes it possible to directly provide the user with an increase in surface areas, which have been achieved by such a therapeutic measure of increasing pressure, both globally based on the global impedance curve or also regionally in each case qualitatively as well as quantitatively, for example in the form of percentages in a win/loss representation or win/loss indication (WIN/LOSS) for further diagnostics and therapy.

FIG. 2 and FIG. 3 show variations according to FIG. 1, the same elements in FIGS. 1, 2, 3 are designated with the same reference numerals in FIGS. 1, 2, 3. In FIGS. 2, 3, embodiments are shown in which at a time of a normalization situation 33, which is temporally prior to the first situation 31 and the second situation 32, at a time to impedance values $Z_0$ or image data 3 are acquired as a normalization data set 330 by the EIT system 30 and are stored as a fourth data set 104. The normalization situation 33 arises in a situation before the start of inspiration or at the end of an expiration. The normalizations in the normalization situations 33 are performed differently by the control unit 70 in FIGS. 2, 3. In FIG. 2, in a system 200, a normalization of the difference 71 determined by the comparison 700 is performed based on the fourth data set 104. Neither the second data set 102 nor the third data set 103 are directly included in the normalization. Such an embodiment according to FIG. 2 can be used as a supplement to the system 100 according to FIG. 1. In FIG. 3, normalizations of the second data set 102, the third data set 103 and all further impedance values 74, 75, image data 3, 39 determined in the course of the data acquisition with the EIT system 30 are performed in a system 300 on the basis of the fourth data set 104 determined during the normalization situation 33. Thus, these normalizations are also indirectly included in the determination of the difference 71, so that the output signal 900 indicates the difference DZ 71 or the corrected difference DZ$_{K1}$ in a form normalized to the normalization situation 33.

FIGS. 4 to 6 show embodiments of FIGS. 1 to 3 of data processing by the control unit 70 as systems 400, 500, 600. Identical elements in FIGS. 1, 2, 3, 4, 5, 6 are designated by the same reference numerals. Common to the described sequences of data processing based on FIGS. 4 to 6 is that in the course of time of ventilation by the ventilation device, a lowering of a pressure level from a second end expiratory pressure level PEEP$_B$ 82 to a third end expiratory pressure level PEEP$_C$ 83 is initiated by the control unit 70. The aspects relating to the control unit 70, the data input unit 50, the data output unit 90, the visualizations 3001, 3002 and also the reading-in and provision of measurement data 4 as a first data set 101 and of EIT data 3, 39 as a second data set 102 and also a third data set 103 are configured in a comparable manner, as described for FIGS. 1 to 3 with the systems 100, 200, 300. The first data set 101 is acquired by the control unit in the same manner as described with respect to FIGS. 1-3, in a continuous manner, i.e. continuously, so that the first data set comprises a plurality of data elements indicating pressure measurement values and a progression of pressure measurement values of the ventilation pressure in the course of ventilation. During operation of the system 400, the control unit 70 performs the data processing described below with a first situation 31 and a second situation 32. For illustration purposes, FIG. 4 schematically shows pressure/time courses of the measuring device 40 during execution of the ventilation with times t$_2$, t$_y$ with associated pressure measurement values P$_2$ 42, P$_y$ 47—in a comparable manner as shown and described with respect to FIGS. 1 to 3. For further illustration, FIG. 4 schematically shows pressure/time courses t$_y$, Z$_2$ 76, Z$_y$ 77, ZGlobal 75 of the EIT system 30 during ventilation—shown and described in comparable manner to FIGS. 1 to 3 in the form of data fields (arrays). In addition, the EIT-data 3, 39 of the two situations 31, 32 are schematically shown in a time lapse of visualizations 3002 of the lungs. During operation of the system 400 according to FIG. 4, the control unit 70 performs the data processing described below based on the first set of data 101, the second set of data 102 and the third set of data 103. In contrast to FIGS. 1 to 3, in FIG. 4, a slightly different functional sequence takes place in the system 400 compared to 800. The positive end-expiratory pressure level (PEEP) is lowered during the second situation 32 compared to the first positive end-expiratory pressure level (PEEP$_B$) 82 by the pressure difference $-\Delta P$ 421 to the third positive end-expiratory pressure level (PEEP$_B$) 83. The control unit 70 uses the predetermined pressure difference $-\Delta P$ 421 in the control signal 72 to lower the pressure of the positive end-expiratory pressure level (PEEP) at the ventilation device 2 according to formula 4.

$$(PEEP_B) - \Delta P = (PEEP_C) \quad \text{Formula 4}$$

The control unit 70 uses the impedance values of the first situation 31 and the impedance values of the second situation 32 or the second set of data 102 and the third set of data 103, as already described with respect to FIG. 1, to determine a difference DZ 71 between the two situations 31, 32 by means of a comparison 800 with a subtraction.

$$DZ = Z_y - Z_2 \quad \text{Formula 5}$$

The pressure measurement value $P_2$ 42 as a data element within the first data set 101 represents a pressure level of an inspiratory ventilation pressure $P_{insp}$ at a time $t_2$ of a rising slope in the course of the ventilation during the second situation 32, wherein the ventilation is performed at the lowered end expiratory pressure level PEEP$_C$ 83 by the ventilation device 2. Also, in this embodiment according to FIG. 4, it is of interest to determine whether the lungs or which areas of the lungs have not only been directly affected by the (pressure reduction) caused volume decrease, but whether and in which areas of the lungs a decrease of lung areas (pulmonary sacs, alveoli) has occurred which were previously available for gas exchange. Such a "closure" of lung areas which were previously available for gas exchange is also referred to as derecruitment or "de-recruitment". For this purpose, in the comparison 800, the pressure situation $P_2$ 42 at the time $t_2$ of the second situation 32, which corresponds in amplitude or magnitude to the second positive end-expiratory pressure level (PEEP$_B$) 82 during the first situation 31, is identified by means of an analysis within the first data set 101. Subsequently, a data set is identified by means of an analysis within the third data set 103 at time $t_2$. This identified data set of impedance values is included in the comparison 800 as a correction data set KDS $Z_{K2}$ 321 of impedance values 77 or image data 39 associated with the pressure situation $P_2$ and at time $t_2$ for some type of normalization. To normalize the difference DZ 71, the correction data set KDS $Z_{K1}$ 321 is applied according to the following formula 6 by the control unit 70 to determine a "loss" (LOSS).

$$LOSS = DZK_2 = Z_y - Z_2 + Z_{K2} \quad \text{Formula 6}$$

The corrected difference LOSS or $DZ_{K2}$ 721 determined in this way may be provided by means of the data output unit 90 as an output signal 900 indicating the difference 721. The output signal 900 may be displayed by means of a schematic visualization 3000. In this schematic visualization 3000, four representative regions I . . . IV (Regions of Interest: ROI) are shown as an example, in this example, a small dark area region is visible in region II. This small dark area II represents a region of the lungs in which a regional decrease in the ventilation of the lungs has occurred during the lowering of the positive end-expiratory pressure level. This means that in this area II, not only has there been a decrease in volume in the lungs caused directly by the reduction in pressure $-\Delta P$, but that regionally there has been a decrease in the amount of lung areas (pulmonary sacs, alveoli) in the lungs which were previously still available for gas exchange.

FIG. 5 and FIG. 6 show variations according to FIG. 4. Identical elements in FIGS. 4, 5, 6 are designated with the same reference numerals in FIGS. 4, 5, 6. In FIGS. 5, 6, embodiments are shown in which at a time of a normalization situation 33, which is temporally prior to the first situation 31 and the second situation 32, at a time to impedance values $Z_0$ or image data 3 are acquired as a normalization data set 330 by the EIT system 30 and stored as a fourth data set 104. The normalization situation 33 arises in a situation before the start of inspiration or at the end of an expiration. The normalizations in the normalization situations 33 are performed differently by the control unit 70 in FIGS. 5, 6. In the FIG. 5, in a system 500, a normalization of the difference 71 determined by the comparison 800 is performed on the basis of the fourth data set 104. Neither the second data set 102 nor the first data set 103 are directly included in the normalization. Such an embodiment according to FIG. 5 can be used as a supplement to the system 400 according to FIG. 4. In FIG. 6, in a system 600, normalizations of the second data set 102, the third data set 103 and all further impedance values 74, 75, image data 3, 39 determined in the course of the data acquisition with the EIT system 30 are performed on the basis of the fourth data set 104 determined during the normalization situation 33. Thus, these normalizations also indirectly enter into the determination of the difference 71, so that the output signal 900 indicates the difference DZ 71 or the corrected difference $DZK_2$ in a form normalized to the normalization situation 33. Further variants in the design of the processes 400 and further possibilities for utilizing the output signal 900 result accordingly, as already described with respect to FIGS. 1-3. With the embodiments described with reference to FIGS. 1-6, it is possible to directly provide the user with a decrease or an increase in surface areas, which are caused by therapeutic measures of pressure increase or pressure decrease, both globally on the basis of the global impedance curve or also regionally in each case qualitatively as well as quantitatively, for example in the form of percentages in a win/loss representation or win/loss indication (WIN/LOSS) for further diagnostics and therapy. In typical embodiments of the systems 100, 200, 300, 400, 500, 600, a predetermined waiting period may be taken into account before acquisition after initiation of the second situation 31 by the control unit 70. Thus, in an optional embodiment, the control unit may take into account a predetermined waiting period 35, for example from 5 to 10 breathing cycles, before impedance values for comparison 700, 800 are used to determine the difference 71, 711, 721. In optional embodiments of the systems 100, 200, 300, 400, 500, 600, in addition to pressure readings 41, 45, flow values 46 or volumes 49 may be provided by the measurement device 40 at the data input unit 50. In this way, assignments of impedance values 74, 75 to tidal volumes as well as inspiratory or expiratory flow rates in the course of ventilation can be made by the control unit 70, which can be advantageous to embodiments or variations as an electroimpedance tomography system, in which the determined impedance values can not only qualitatively determine and visualize their relative changes, but can also process volumes and volume changes in the course of ventilation to quantitative observations. In particular, if the measurement system 40 is configured as a part of the ventilation device 2, corresponding measured values or data on flow rates or volumes are mostly available. In optional embodiments of the systems 100, 200, 300, 400, 500, 600 according to FIGS. 1, 2, 3, 5, 6, normalizations can be performed prior to each breathing cycle before the start of inspiration, for example at the minimum of the global impedance curve, but the normalization can also be performed less frequently, for example every 5 to 10 breathing cycles. In alternative embodiments of the systems 100, 200, 300, 400, 500, 600 of FIGS. 1 to 6, instead of predetermining the pressure measurement values $P_1$ 41 or $P_2$ 42 during the first situation 31 to form the second positive end-expiratory pressure level ($PEEP_B$) 82, ($PEEP_C$) 83, an alternative sequence can also be configured, in which the second situation 32 is given temporally before the first situation 31—as already indicated previously with regard to the temporal relationship between the first and second situations 31, 32. This alternative sequence can in turn also be explained with reference to the illustrations according to FIGS. 1 to 6.

In alternative sequences, exemplarily described here for a sequence according to FIGS. 1-3, a value of end expiratory pressure (PEEP) is determined within the first data set 101 in the second situation 32. Subsequently, within the first data set 101, the pressure measurement value $P_1$ 41 during a rising slope of the inspiratory ventilation pressure $P_{insp}$ above the first positive end expiratory pressure level ($PEEP_A$) 81 in the first situation 31 is identified and determined during the course of ventilation. By means of the pressure measurement value $P_1$ 41, the time $t_1$ within first data set 101 is thus identified in a retrospective manner, as it were. Next, a data set of impedance values is determined within the second data set 103 at the time $t_1$, which corresponds to the second end-expiratory pressure level ($PEEP_B$) 82 during the course of ventilation.

In alternative embodiments of the systems 100, 200, 300, 400, 500, 600 of FIGS. 1 to 6, this identified data set of impedance values can be included in the comparison 700 or comparison 800 as a correction data set KDS $Z_{K1}$ 311 or $Z_{K2}$ 321 associated with the pressure situation $P_1$ and at the time $t_1$, as described in the explanations of FIGS. 1-3 or 4-6. By means of the output signal 900, the result of the comparison 700, 800 can be further utilized to form a profit/loss representation or profit and loss indication (WIN/LOSS).

Figure 7:
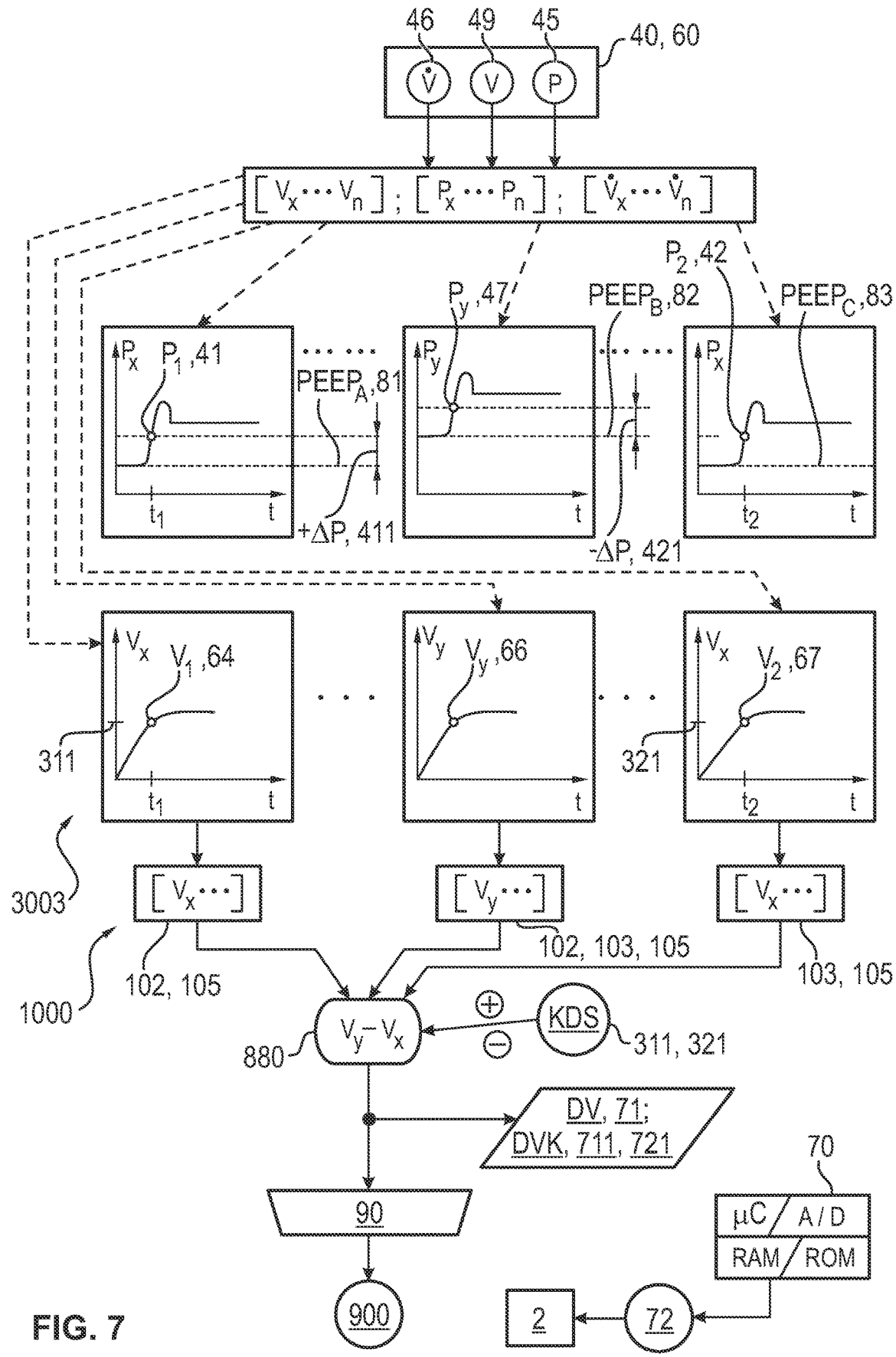
FIG. 7 is a schematic representation of elements for data processing of measurement data or data sets.

FIG. 7 shows a schematic representation of elements for data processing of measured data or data sets as a system 1000 with a measuring device 40, a control unit 70, a data output unit 90, a data input unit 50 and an analysis device in one embodiment, in which the analysis device 30 according to FIGS. 1-6 is configured as a device 60 for determining and providing a first data set 101 of pressure measured values 45 and a fifth data set 105 of flow measured values 46, volume measured values 49. Identical elements in FIGS. 1, 2, 3, 4, 5, 6, 7 are designated by the same reference numerals in FIGS. 1, 2, 3, 4, 5, 6, 7. The fifth data set 105 can be allocated by the control unit 70 according to the situation into a second data set 102 and a third data set 103, as described with respect to FIG. 1, that is, to the first situation 31 and to the second situation 32, respectively. In this FIG. 7, the device 60 is configured with the measuring device 40 as a common device 40, 60. Data of the fifth data set 105 are shown as volumes 67 in a time lapse in visualizations 3003. Situations of inspiratory ventilation pressures $P_{insp}$ with pressure readings $P_1$, 41, $P_y$, 47, $P_2$ 42 in a time course with time points $t_1$, $t_2$ on rising slopes of the inspiratory pressure $P_{insp}$ at different pressure levels of the end-expiratory pressure $PEEP_A$, $PEEP_B$, $PEEP_C$ 81, 82 83 are shown. The pressure levels of end-expiratory pressure $PEEP_A$, $PEEP_B$, $PEEP_C$ 81, 82 83 differ in pressure differences $+\Delta P$ 411, $-\Delta P$ 421. A comparison 880 includes volume readings of the fifth data set 105 and pressure readings of the first data set 101 of the two situations and a correction data set KDS 311, 321 specific to the situation to determine a difference DV 71. The correction data set KDS 311, 321 includes volumes or volume readings corresponding to time points $t_1$, $t_2$ in the time course of inspiratory pressure $P_{insp}$. At time $t_1$ with the pressure measurement value $P_1$ 41 of the inspiratory ventilation pressure $P_{insp}$, a volume 64 that has flowed in summarily since the beginning of the inhalation phase up to this time $t_1$ corresponds as correction data set KDS 311. At the time $t_2$ with the pressure measurement value $P_2$ 42 of the inspiratory ventilation pressure $P_{insp}$, a volume 67 that has flowed in summarily since the beginning of the inhalation phase up to this time $t_2$ corresponds as correction data set KDS 321. The difference DV 71 or the corrected difference, $DVK_1$ 711 or $DVK_2$ 721 determined on the basis of the correction data set KDS 311, 321 can be provided as an output signal 900 by means of the data output unit 90.

Figure 8:
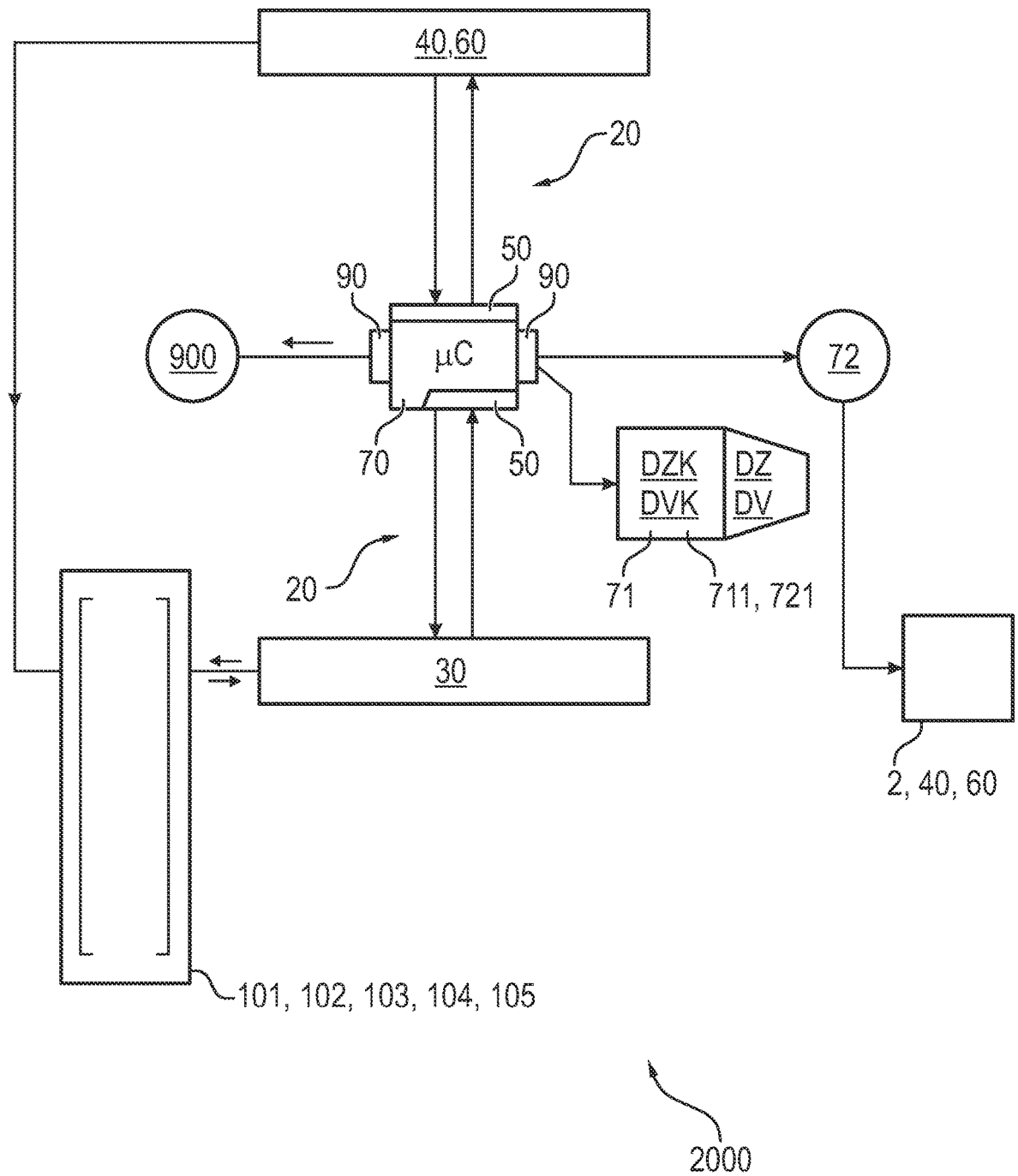
FIG. 8 is a schematic representation of a system for ventilation and monitoring of a living being.

FIG. 8 shows a common system 2000 for ventilation and monitoring of a living being with analysis device 30, 60, measuring device 40, control unit 70, data output unit 90, data input unit 50, ventilation device 2. Identical elements in FIGS. 1, 2, 3, 4, 5, 6, 7, 8 are designated with the same reference numerals in FIGS. 1, 2, 3, 4, 5, 6, 7, 8. The data processing by the control unit 70 of the data sets 101, 102, 103, 104, 105 results in a comparable form as described with respect to FIGS. 1-7. A difference 71 or a corrected difference 711, 721 is determined and provided by the control unit based on the data sets 101, 102, 103, 104, 105, as explained and described with respect to FIGS. 1-7. The control unit can be centrally arranged in the system or modularly distributed and arranged in the system 2000, both as a module or sub-module of analysis device 40, 60, measurement device 40, control unit 70, data output unit 90, data input unit 50, ventilation device 2 as well as a central control unit. Splits in master/slave configurations are possible in the system 2000. The system 2000 can have a network (LAN, WLAN, Ethernet) or a bus system (RS232, CAN bus, $I^2$ C bus, SPI, USB, SCSI, IEEE488) as interfaces 20, via which the components 2, 30, 40, 50, 60, 70, 90 can be connected for unidirectional or bidirectional data exchange in the system. The joint system 2000 for ventilation and monitoring of a living being may enable coordinated and controlled weaning of a living being from ventilation. To this end, the control unit 70 may initiate, coordinate, or control a maneuver for weaning by means of the control signal 72. In a weaning maneuver, a gradual or stepwise pressure reduction of the inspiratory ventilation pressure $P_{insp}$ and/or expiratory ventilation pressure $P_{exp}$ and/or end expiratory pressure PEEP is performed by the ventilation device 2 in the course of the ventilation. In this regard, the control unit 70 may initiate, coordinate or control the steps or stages of pressure reduction by means of the control signal at a level of the stages of pressure reduction or a time interval between steps of pressure reduction depending on the detected difference 71, 711, 721 at the ventilation device.

Initiating enables the control unit 70 to trigger or activate active elements, actuators such as ventilation drives (blowers, pistons, pumps), actuating and switching elements, dosing elements, for example valves in the ventilation device 2. Coordinating enables the control unit 70 in the system 2000 to coordinate measurement acquisition, inclusion of sensors or actuators, data processing and activation of the actuating and switching elements.

Controlling enables the control unit 70 to control (open loop control), for example, an adjustment or setting of certain analog, digital or logical states of the actuating and switching elements. A control enables the control unit 70 to provide a closed loop control by means of adjustment or setting of certain analog, digital or logical states of the actuating and switching elements in a closed control loop and a configuration of a closed loop control or a controller of a certain type, for example as a P-controller PI-controller, PID-controller with certain properties (gain $K_P$, reset time $T_N$, derivative time $T_V$).

For an implementation of a weaning process in ventilation, it may be very advantageous in embodiments according to FIGS. 1 to 8 if the ventilation device 2 comprises the analysis device 30, 60, the measuring device 40, the control unit 70, the data output unit 90, the data input unit 50 and thus the system forms the common system 2000 as well as the systems 100, 200, 300, 400, 500, 600.

While specific embodiments of the invention have been shown and described in detail to illustrate the application of the principles of the invention, it will be understood that the invention may be embodied otherwise without departing from such principles.

LIST OF REFERENCE NUMBERS

| | |
|---|---|
| 100, 200, 300 | System |
| 400, 500, 600 | System |
| 2 | Ventilator device |
| 3, 39 | Image data |
| 4 | Measured data |
| 20 | Interfaces, bus system, data bus, network, Ethernet |
| 30 | EIT system |
| 31 | First situation |
| 32 | Second situation |
| 33 | Normalization situation |
| 35 | Waiting time |
| 40 | Measuring device |
| 46 | Flow readings |
| 41 | Pressure reading $P_1$ |
| 45 | Pressure sensor, pressure readings |
| 411 | Predetermined pressure difference + $\Delta P$ |
| 421 | Predetermined pressure difference − $\Delta P$ |
| 50 | Data input unit |
| 60 | Volume measuring device |
| 64 | Volume measured values $V_1$ |
| 66 | Volume measured values $V_y$ |
| 67 | Volume measured values $V_2$ |
| 70 | Control unit |
| 71 | Difference DZ, DV |
| 711, 721 | Corrected difference DZK, DVK |
| 72 | Control signal |
| 73 | Region of interest, representative area (ROI) |
| 74 | Impedance value $Z_1$ |
| 75 | Global impedance curve, ZGlobal |
| 76 | Impedance value $Z_2$ |
| 77 | Impedance values $Z_y$ |
| 81 | First $PEEP_A$ Level A |
| 82 | Second $PEEP_B$ Level B |
| 82 | Third $PEEP_C$ Level C |
| 90 | Data output unit |
| 101 | First data set |
| 102 | Second data set |
| 103 | Third data set |
| 104 | Fourth data set |
| 105 | Fifth data set |
| 3000, 3001, 3002, 3003 | Visualizations |
| 311, 321 | Correction data set KDS |
| 330 | Normalization data set NDS, representative ref. value $Z_0$ |
| 700, 800, 880 | Comparison |
| 900 | Output signal |
| 1000 | System |
| 2000 | Common system |

What is claimed is:

1. A system for use during a ventilation by a ventilation device to process data obtained by means of an analysis device suitable for determining a lung condition and to process measurement data obtained by a measuring device suitable for a metrological acquisition of physical measurement data, the system comprising:
   a data input unit configured to acquire measuring device data or to receive measuring device data of the measuring device, which measuring device data are assignable to situations with predetermined pressure levels to provide the measuring device data as a first data set of measurement data over a time course of an observation period during a ventilation of a living being and the data input unit being configured to acquire data or to receive data from the analysis device which can be assigned to a first situation to provide the data as a second set of data over a time course of the observation period during ventilation of a living being, and data input unit being configured unit to acquire further data or receive further data from the analysis device which can be assigned to a second situation, in order to provide the further data as a third data set over a time course of at least one location over the observation period during ventilation of a living being;
   a data output unit; and
   a control unit configured to:
   provide a control signal by interaction between the control unit and the data output unit;
   initiate an adjustment by a predetermined pressure difference from a first positive end expiratory pressure level to a second positive end expiratory pressure level at the ventilation device by means of the control signal;
   process the first data set, the second data set and the third data set to determine, by a comparison, a difference between the further data of the second situation and the data of the first situation;
   include in the comparison a correction data set for a correction of the difference, the correction data set comprising data elements of the second data set which indicates specific pressure situations at times t1, t2 within the observation period, determine, based on the comparison and the difference or based on the corrected difference, an output signal which indicates the difference and/or the corrected difference; and
   provide the output signal with the data output unit.

2. A system according to claim 1, wherein the second data set comprises data elements which indicate certain pressure situations at times t1, t2 as to a rising slope of an inspiratory ventilation pressure and/or a falling slope of an expiratory ventilation pressure.

3. A system according to claim 1, wherein the analysis device is configured and adapted for imaging the lungs of a living being.

4. A system according to claim 3, wherein the analysis device is configured as at least one of:
   a device configured to image the lungs of a living being for electrical impedance tomography or an EIT system;
   a device configured to image the lungs of a living being for magnetic resonance tomography;
   a computer tomography device configured to image the lungs of a living being;
   an apparatus for ultrasound imaging of the lungs of a living organism.

5. A system according to claim 1, wherein the analysis device is configured to determine a volume of the lungs of a living being.

6. A system according to claim 1, wherein:
the first situation is assignable to a first predetermined pressure level:
an adjustment of a first positive end-expiratory pressure level based on the control signal to a second positive end-expiratory pressure level by a predetermined pressure difference is initiated as an increase by the predetermined pressure difference at the level of the predetermined pressure level at the ventilation device;
the control unit is configured to perform said comparison as a subtraction $(Z_y-Z_1)$ of the third data from the second data;
the control unit is configured to perform said correction as a subtractive correction based on a correction $(Z_{K1})$ to determine a corrected difference $(DZK_1)$, with $DZK_1=(Z_y-Z_1)-Z_{K1}$.

7. A system according to claim 1, wherein:
the second situation is assignable to a second predetermined pressure level;
an adjustment of a first positive end-expiratory pressure level based on the control signal to a third positive end-expiratory pressure level by a predetermined pressure difference is initiated as a reduction by the predetermined pressure difference at the level of the predetermined pressure level at a ventilation device;
the control unit is configured to perform the comparison as a subtraction $(Z_y-Z_2)$ of the third data set from the second data set;
the control unit is configured to perform said correction as an additive correction based on a correction $(Z_{K2})$ to determine a corrected difference $(DZK_2)$, with $DZK_2=(Z_y-Z_2)+Z_{K2}$.

8. A system according to claim 6, wherein the control unit is adapted to perform during the first situation the data acquisition at the predetermined pressure level while performing the ventilation.

9. A system according to claim 7, wherein the control unit is adapted to perform the data acquisition during the second situation at the predetermined pressure level while performing the ventilation.

10. A system according to claim 6, wherein the control unit is adapted to perform the data acquisition during the first situation at the predetermined pressure level on a plateau of the inspiratory ventilation pressure temporally after a rising slope of the inspiratory ventilation pressure.

11. A system according to claim 7, wherein the control unit is adapted to perform the data acquisition during the second situation at the predetermined pressure level on a plateau of the inspiratory ventilation pressure temporally after a rising slope of the inspiratory ventilation pressure.

12. A system according to claim 1, wherein the measuring device is adapted to carry out at least one of:
a pressure measurement;
a flow measurement; and
a volume measurement.

13. A system according to claim 1, wherein the control unit is configured to perform the data acquisition as an acquisition of impedance values of selected or representative areas of the lungs and/or as an acquisition of global impedance values over time as a global impedance curve.

14. A system according to claim 1, wherein the control unit is configured to:
determine a representative reference value or a fourth data set of reference values as a normalization data set by means of a further data acquisition in a normalization situation temporally before the first situation; and
to carry out normalization during data acquisition based on the normalization data set and/or based on the representative reference value.

15. A system according to claim 1, wherein the control unit is configured to perform a data adjustment to compensate for time differences between the first data set and the second data set to synchronize the measuring device and the analyzing device in time.

16. A system according to claim 1, wherein the control unit is configured to perform a start of data acquisition during the second situation after a time delay.

17. A system according to claim 16, wherein the control unit is configured to perform the data acquisition during the second situation in a predetermined time interval of 5 to 10 breathing cycles after initiation of the second situation with increase to a second positive end-expiratory pressure level.

18. A system according to claim 16, wherein the control unit is configured to perform the data acquisition during the second situation in a predetermined time interval of 5 to 10 breathing cycles after initiation of the second situation with lowering to a second positive end-expiratory pressure level.

19. A system according to claim 1, wherein the control unit is configured to initiate a maneuver with a substantially constant pressure level with the first situation on the ventilation device in the course of ventilation.

20. A system according to claim 1, wherein the control unit is adapted, during the performance of ventilation, to initiate a maneuver at the ventilation device with a plurality of discretely formed pressure levels on a rising slope of the inspiratory ventilation pressure.

21. A system according to claim 1, wherein the measuring device is formed as a module or as a component of the ventilation device.

22. A system according to claim 1, wherein the system is provided in combination with the analyzing device, the measuring device and the ventilating device to form a common living being ventilating and monitoring system.

23. A system according to claim 22, wherein the control unit is a component or submodule in one or more of the ventilation device, the analysis device and the measuring device and is formed as a component or module of the common system.

24. A system according to claim 22, wherein the control unit is configured to initiate maneuvers with multiple pressure levels of inspiratory ventilation pressure at the ventilation device during the performance of ventilation.

25. A system according to claim 22, wherein the control unit is adapted, in a procedure or maneuver for weaning a living being from ventilation with a pressure reduction of inspiratory ventilation pressure and/or expiratory ventilation pressure and/or end expiratory pressure by the ventilation device to initiate, coordinate or control the steps or stages of pressure reduction by means of the control signal at a level of the stages of pressure reduction or a time interval between steps of pressure reduction based on the difference.

26. A system according to claim 22, wherein the control unit is configured to initiate a maneuver with a predetermined slower inspiratory pressure increase prior to or with the first situation on the ventilation device in the course of ventilation.

27. A system according to claim 22, wherein the control unit is configured to initiate an increase of the sampling rate during data acquisition at the beginning of the first situation at the measuring device and/or at the analysis device.

28. A process for processing data, the process comprising the steps of:
- receiving measurement data which can be assigned to situations with predetermined pressure levels;
- providing the measurement data as a first data set;
- receiving electroimpedance tomography (EIT) data in a first situation;
- providing the EIT data as a second data set;
- receiving further EIT data in a second situation;
- providing the further EIT data as a third data set;
- processing the first data set, the second data set and the third data set to determine a difference between the further EIT data of the second situation and the EIT data of the first situation by means of a comparison including a correction data set; and
- providing an output signal indicating the difference and/or a corrected difference.

* * * * *